(12) United States Patent
Chang et al.

(10) Patent No.: US 7,326,326 B2
(45) Date of Patent: Feb. 5, 2008

(54) SYSTEM AND METHODS FOR ELECTROPHORETIC SEPARATION OF PROTEINS ON PROTEIN BINDING MEMBRANES

(75) Inventors: Frank N. Chang, Dresher, PA (US); Christopher R. Yonan, Plymouth Meeting, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 799 days.

(21) Appl. No.: 10/659,003

(22) Filed: Sep. 9, 2003

(65) Prior Publication Data

US 2004/0121488 A1    Jun. 24, 2004

Related U.S. Application Data

(60) Provisional application No. 60/409,796, filed on Sep. 11, 2002.

(51) Int. Cl.
*G01N 27/453* (2006.01)
*G01N 27/447* (2006.01)

(52) U.S. Cl. .................. 204/546; 204/600; 204/641; 204/450

(58) Field of Classification Search ............... 204/450, 204/546, 600, 641, 642
See application file for complete search history.

(56) References Cited

U.S. PATENT DOCUMENTS

| | | | |
|---|---|---|---|
| 3,930,973 A * | 1/1976 | Nerenberg | 204/546 |
| 3,984,298 A | 10/1976 | Haber | 204/180 |
| 4,128,470 A * | 12/1978 | Hiratsuka et al. | 204/641 |
| 4,146,454 A | 3/1979 | Haber | 204/180 |
| 4,909,918 A * | 3/1990 | Bambeck et al. | 204/619 |
| 5,068,019 A * | 11/1991 | Yoshida et al. | 204/546 |
| 5,137,609 A * | 8/1992 | Manian et al. | 204/452 |
| 5,264,098 A | 11/1993 | Chevigné | |
| 5,314,595 A | 5/1994 | Fuller | |
| 5,637,202 A * | 6/1997 | Harrington et al. | 204/469 |
| 6,866,772 B2 * | 3/2005 | Selai et al. | 208/327 |

OTHER PUBLICATIONS

Hong et al, Hwahak Konghak, 29(4), Aug. 1991, pp. 457-462.*
Lederer, An Introduction to Paper Electrophoresis and Related Methods, 1955, pp. 23-30.*
Allen et al, International Journal of Pharmaceutics 187, 1999, pp. 259-272.*
Certified translation of Hong et al, Hwahak Konghak, 29(4), Aug. 1991, pp. 457-462.*
International Search Report dated Aug. 3, 2004 in PCT/US03/28359.

(Continued)

*Primary Examiner*—Kaj K. Olsen
(74) *Attorney, Agent, or Firm*—Drinker, Biddle & Reath LLP

(57) ABSTRACT

Proteins can be rapidly separated to a high degree of resolution by electrophoresis on polymeric membranes that have high protein binding capacity. The electrophoretic separation is carried out in a low conductivity, water-miscible organic solvent buffer. The low conductivity of the organic solvent buffer minimizes heat generation, and the water-miscible nature of the organic solvent buffer permits the analysis of hydrophobic and low molecular weight proteins as well as hydrophilic proteins. When electrophoresis is conducted under non-denaturing conditions, it allows the detection of enzymatic activities, protein-protein interactions and protein-ligand interactions.

93 Claims, 11 Drawing Sheets

OTHER PUBLICATIONS

JPO abstract of JP 63-262550 A (Yoshida et al.), Oct. 28, 1988.
JPO abstract of. JP 06-130033 A (Gurske et al.) May 13, 1994.
Haber; "*Chemoelectronic mobilization of chemical species in low-conductivity fluids: New electrokinetic effect*" *Proc. Natl. Acad. Sci. USA* 79:272-276 (Jan. 1982).

Heller, et al.: "*Membrane electrophoresis of DNA*" *Electrophoresis* 14:162-164 (1993), month unknown.
Haber: "*Electromolecular propulsion (EMP): a rapid, simple method for analyzing dyes used in microscopy*" *Biotechnic & Histochemistry* 73(2):59-69 (Feb. 1998).

* cited by examiner

FIG. 4A PVDF
FIG. 4B Hybond-N
FIG. 4C Hybond NX
FIG. 4D Hybond-N+
FIG. 4E Hybond-XL
FIG. 4F Whatman 3

SYSTEM AND METHODS FOR ELECTROPHORETIC SEPARATION OF PROTEINS ON PROTEIN BINDING MEMBRANES

CROSS-REFERENCE TO RELATED APPLICATION

The application claims the benefit of co-pending U.S. provisional patent application No. 60/409,796, filed on Sep. 11, 2002.

FIELD OF THE INVENTION

The invention relates to the field of electrophoretic separation of molecules, in particular the separation of proteins by electrophoresis through polymeric membranes.

BACKGROUND OF THE INVENTION

Recent evidence shows that the human genome contains approximately 35,000 different genes. Due to post-translational modifications, the human "proteome," or the number of proteins produced by these genes, probably numbers in the hundreds of thousands. Much study and effort will be needed to unravel the complete complement and function of the human proteome.

A basic tool for analyzing proteins from the human proteome (and other sources) is electrophoresis. Electrophoresis is a method by which molecules are moved through a porous support or substrate by the application of an electric current. Using this method, a mixture of charged molecules can be separated on the basis of their physical characteristics (e.g., molecular weight or "$M_r$") and/or their chemical nature (e.g., charge or isoelectric point) by movement of charged species through an electrolytically conductive medium.

One dimensional ("1-D") electrophoresis is a standard technique in which molecules are forced to migrate along one axis in a separation substrate. 1-D electrophoretic analysis of proteins is typically performed in a gel matrix (such as polyacrylamide) under denaturing conditions; i.e., using ionic or non-ionic detergents. The detergent used to denature the proteins induces a random configuration and can impart a relatively constant charge/mass ratio to the protein molecules. Under these conditions, the relative mobility of the denatured protein decreases almost linearly with an increase in $\log(M_r)$. If protein binding or biological activity is to be preserved, the electrophoresis can be performed under "non-denaturing" conditions, which allow the proteins to retain their native form. Under non-denaturing conditions, relative mobility of proteins is a function of both $M_r$ and charge. However, the resolution of proteins electrophoresed through gels under non-denaturing conditions is usually poor.

Two-dimensional polyacrylamide gel electrophoresis ("2-D PAGE"), first developed by O'Farrell (*J. Biol. Chem.* 250:4007-4021, 1975), is another widely used method for separating and analyzing proteins. In this method, proteins are separated in the first dimension according to their isoelectric points in the presence of pH gradient generated by using ampholytes or similar materials. This is followed by separating the proteins according to their molecular weights in a second dimension. The proteins are typically electrophoresed in the first dimension under denaturing conditions which do not impose a uniform charge/mass ratio; for example, in the presence of 9M urea. Electrophoresis in the second dimension is typically performed in the presence of an ionic detergent such as SDS, and is analogous to the denaturing 1-D electrophoresis discussed above. Protein-protein interactions or biological activities of the separated proteins are not preserved in conventional 2-D PAGE techniques.

A major impediment in the progress of "proteomics," or the analysis of the functions of proteins in a cell, is the complexity and the length of time required for the separation of protein molecules. The conventional 2-D PAGE techniques mentioned above involve multiple steps and generally take one to two days to complete. For example, a typical 2-D PAGE protocol includes: 1) preparation of a gel matrix with a specific pH gradient for performing the first dimensional isoelectric focusing (IEF) step, and the "running" of the IEF gel in the first dimension; 2) equilibration of the IEF gel in the buffer used for the second dimension run, and 3) the transfer of proteins from the IEF gel onto the second dimension slab gel and subsequent running of the second dimension electrophoresis. Although preformed IEF gel strips with a specific pH gradient are commercially available, such strips are typically provided dry and require a rehydration step of 10-12 hours prior to use.

Efficient separation of molecules by 1-D or 2-D electrophoresis requires that all molecules of the same substance have equal velocity during the separation process. To achieve this, the electric field, and therefore the conductivity, must be uniform throughout the volume of the separation medium. The conductive characteristics of the molecules being separated, however, cause the conductivity of the medium to become nonuniform. In practice, a uniform electric field is approximated by using an electrophoretic separation medium and buffer with a high conductivity relative to the conductivity contribution of the molecules being separated. Highly conductive electrophoretic separation media and buffers are typically water-based.

Application of an electric current to highly conductive electrophoretic media and buffers produces large amounts of heat. If not dissipated or reduced, this heat can interfere with the separation process, destroy the molecules being separated, and damage the electrophoretic equipment. Heat generation can be reduced by applying a lower voltage across the electrodes of the electrophoresis unit. However, using a lower voltage increases the overall separation time for the molecules. Alternatively, the heat can be dissipated by using a large volume of electrophoresis buffer as a heat sink, or by direct cooling of the electrophoresis buffer. Either of these techniques increases the cost, complexity and size of the electrophoretic separation apparatus.

Aqueous electrophoresis media are also unsuited for separating hydrophobic proteins (e.g., biologically important cell membrane proteins) and some low molecular weight proteins (e.g., $M_r \leq 10,000$). Such proteins could be separated using organic solvent buffers. As organic solvent buffers are typically of low to medium conductivity, the problems of heat generation discussed above might also be alleviated. However, difficulties in polymerizing some gels in organic solvents, and the incompatibility of organic solvent buffers with many gel electrophoresis systems, have greatly limited the use of such buffers in protein electrophoresis.

A 1-D electro-separation has been developed which uses water-miscible organic solvents to separate small molecules on separation substrates such as filter paper (see U.S. Pat. No. 4,146,454; Haber N., *PNAS USA*, 79:272-276, 1982; and Haber N., *Biotechnic & Histochemistry*, 73: 59-70, 1998). This system is called "electro-molecular propulsion" or "EMP." In EMP, nonpolar or uncharged compounds (such as aromatic hydrocarbons) are induced to migrate through the separation substrate once a threshold current level is passed.

Unlike conventional electrophoresis systems, movement of molecules by EMP does not depend on ionic species dissolved in an electrolytically conductive medium. See Haber N., *Biotechnic & Histochemistry*, 1998, supra. Rather, EMP induces the migration of nonpolar or uncharged compounds by "charge transfer" effects that impose electronic charges on the molecules by an unknown mechanism. The EMP "charge-induced" molecules respond electrokinetically to an applied electrical field, resulting in migration of the molecules.

The EMP technique appears useful for separating small nonpolar molecules such as dye compounds. However, it is not clear whether EMP is suitable for analysis of ampholytic biopolymers such as proteins, even though albumin, hemoglobin, myoglobin, cytochrome C and chymotrypsinogen have been separated on Whatman No. 3 filter paper using this technique (Haber N., *PNAS USA*, 1982, supra). Also, the filter papers and other substrates used in the EMP process do not bind proteins well, and proteins separated by EMP begin to diffuse on the substrates almost immediately after cessation of the electric current. The diffusion of proteins has greatly limited the usefulness of the EMP process, and no 2-D protein separation procedure employing filter papers has been reported.

Proteins separated by conventional electrophoretic techniques are often "blotted" or transferred onto high protein binding capacity, low porosity membranes made from nitrocellulose, nylon, polyvinylidene difluoride (PVDF) or other protein-binding polymers. The blot membranes are then subjected to staining, immunodetection (e.g., Western blot), mass spectrometry, amino acid sequence analysis and other operations. The blotting step is time consuming, and can result in an inefficient transfer of the separated proteins. For example, the retention of low molecular weight proteins by nitrocellulose is influenced by the presence of methanol in the transfer buffer (Pluskal et al., *Biotechniques* 4:272-283, 1986). Higher molecular weight proteins are also known to have lower transfer efficiency onto blotting membranes.

What is needed, therefore, is a high speed, high resolution electrophoresis system that employs organic solvent buffers compatible with hydrophilic, hydrophobic and low molecular weight proteins. The organic solvent buffers should preferably be non-denaturing to preserve protein binding interactions and biological activities, and should have low conductivity so as to minimize heat generation during electrophoretic separation. What is also needed is a separation substrate which minimizes diffusion of the molecules after electrophoresis is completed, and which eliminates the need for transferring the separated molecules from the separation matrix onto a blotting membrane.

SUMMARY OF THE INVENTION

It has now been found that proteins can be electrophoretically separated in both one- and two-dimensions on polymeric membranes that exhibit high protein binding capacity. The electrophoretic separation is carried out in a low conductivity, water-miscible organic solvent buffer. As the buffer is not aqueous-based, both hydrophobic and small molecular weight proteins can be readily separated. The low conductivity of the organic solvent buffer also minimizes heat generation during electrophoretic separation. Consequently, enough voltage can be applied to the present electrophoresis system that separation of molecules is effected in only a fraction of the time required for traditional aqueous electrophoresis systems. Moreover, as protein separation is carried out directly on the blotting membrane, there is no need for the subsequent transfer of separated proteins.

The invention therefore provides an electrophoresis system for the separation of proteins, comprising at least one low conductivity organic solvent buffer, a polymeric membrane having high-protein binding capacity that is compatible with the organic solvent buffer, and an electrophoresis apparatus. The electrophoresis apparatus comprises at least one electrophoresis unit for containing the buffer and membrane, and a power supply capable of generating an electric current in the electrophoresis unit.

In one embodiment, an electrophoresis unit of the electrophoresis system comprises two independent buffer chambers, which are bridged by a pair of plates having a membrane and wick sandwiched between them. Because the buffer chambers are independent, the size of the electrophoresis unit can be varied depending on the size of the plates holding the membrane and wick. As the wick is longer than the plates, the ends of the wick extend into the buffer chambers when the electrophoresis unit is assembled.

The invention also provides a method for the electrophoretic separation of proteins. In the method, at least one low conductivity organic solvent buffer and a polymeric membrane having a high-protein binding capacity that is compatible with the organic solvent buffer are provided. A sample comprising proteins to be separated is then applied to the to the membrane, and the proteins are separated by electrophoresis.

The invention further provides a method for performing two-dimensional membrane electrophoresis. In the method, an electrophoresis system is provided that comprises 1) a first low conductivity organic solvent buffer having a first pH and a second low conductivity organic solvent buffer having a second pH; 2) a polymeric membrane having a high protein binding capacity and which is compatible with the first and second organic solvent buffers; and 3) an electrophoresis apparatus comprising at least one electrophoresis unit for containing the first and second organic solvent buffers and the membrane. A sample comprising proteins to be separated is applied to the membrane, and the membrane is placed in the electrophoresis unit in a first orientation. The first organic solvent buffer is added to the electrophoresis unit, and the proteins are separated in a first dimension by generation of an electric current in the electrophoresis unit. After the first dimension separation is complete, the first organic solvent buffer is removed from the electrophoresis unit and replaced with the second organic solvent buffer. The membrane, which has been equilibrated with the second organic solvent buffer, is then placed in the electrophoresis unit in a second orientation. The proteins which had been separated on the membrane in the first dimension are then separated in a second dimension by generation of an electric current in the electrophoresis unit.

DEFINITIONS

As used herein, "protein" refers to a molecule comprising at least two amino acid residues covalently linked by peptide bonds or modified peptide bonds (e.g., peptide isosteres). No limitation is placed on the maximum number of amino acids which may comprise a protein. The amino acids comprising the proteins referred to herein are understood to be either D- or L-amino acids, with L-amino acids being preferred. In addition, the component amino acids may be β-amino acids, or custom synthesized amino acids or peptidomimetic fragments, e.g. a Friedinger γ lactam, a peptoid or the like, or mixtures of any of these substances.

The proteins referred to herein may also be associated with one or more other molecules, including one or more other proteins, or with one or more metal atoms or metal complexes such as, for example a zinc finger protein. For example, a protein may comprise a homo- or heteromultimeric protein, an antibody/antigen complex, or a ligand/receptor complex. As used herein, the association of a protein with another protein or non-protein molecule is termed a "protein-binding interaction." The proteins referred to herein may also exhibit biological activities; e.g., enzymatic activities.

The proteins referred to herein may contain modifications. Such modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for example, *Proteins—Structure and Molecular Properties*, 2nd Ed., T. E. Creighton, W. H. Freeman and Company, New York, 1993; Wold F, Posttranslational Protein Modifications: Perspectives and Prospects, pgs. 1-12 in *Posttranslational Covalent Modification of Proteins*, B. C. Johnson, Ed., Academic Press, New York, 1983; Seifter et al., "Analysis for protein modifications and nonprotein cofactors," *Meth. Enzymol.* (1990) 182: 626–646; and Rattan et al. (1992), "Protein Synthesis: Posttranslational Modifications and Aging," *Ann NY Acad Sci* 663: 48-62, the entire disclosures of which are herein incorporated by reference.

DETAILED DESCRIPTION OF THE INVENTION

Figure 1:
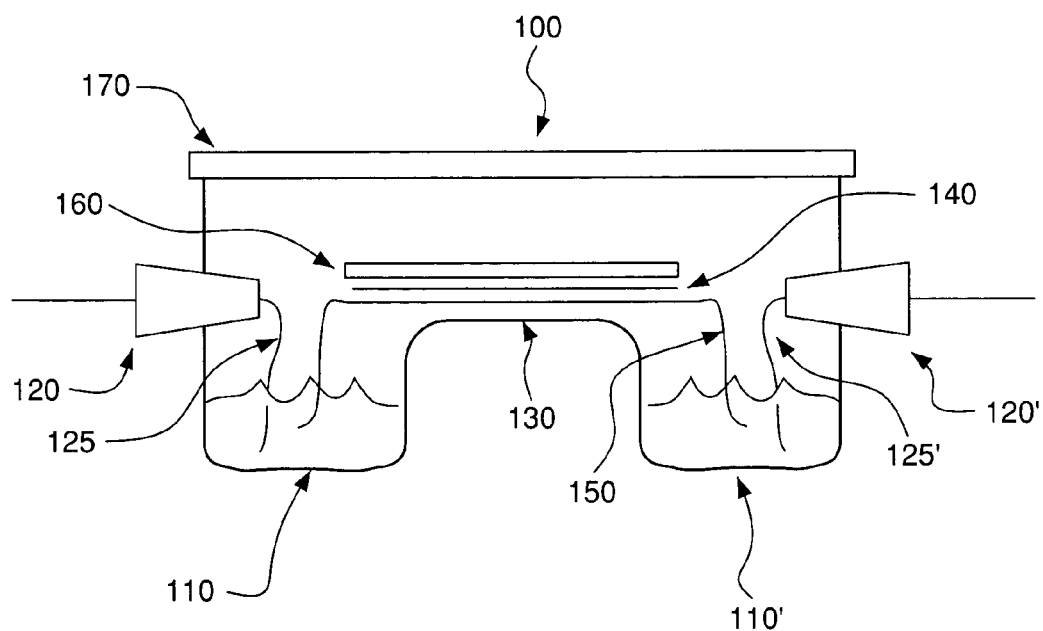
FIG. 1 is a side cutaway view of a horizontal electrophoresis unit of the invention.

The present "membrane electrophoresis" system and methods allow the rapid, high resolution separation of proteins directly on polymeric membranes. The membrane electrophoresis system and methods of the invention are simple and versatile, and can be used in any application for which conventional gel electrophoresis is normally used. For example, membrane electrophoresis can be used to separate protein samples for analytical purposes, to identify the nature of specific proteins, to assess the purity of proteins, and the like.

The membrane electrophoresis of the present invention can be carried out under non-denaturing conditions, thus allowing the retention of protein-binding interactions and enzymatic activities. The present membrane electrophoresis can also be performed under denaturing conditions (e.g., in the presence of urea).

All percentages referred to herein are by volume, unless otherwise indicated.

The electrophoresis buffers for use in membrane electrophoresis comprise water-miscible organic solvents which have been formulated to exhibit low conductivity. As used herein, an organic solvent buffer has "low conductivity" when the buffer produces a current of about 0.0001 mA/cm$^2$ membrane to about 0.2 mA/cm$^2$ membrane when subjected to a fixed voltage (e.g., 3.5 kV) One of ordinary skill in the art can readily determine the conductivity of an organic solvent buffer using techniques known in the art. A convenient technique for measuring conductivity of buffers for use in the present invention is to electrophorese a protein sample on a 1 cm by 8 cm membrane at 3.5 kV, as described in Example 2 below.

The present low conductivity organic solvent buffers comprise one or more high boiling point organic solvents that exhibit little to no conductivity. Such solvents are referred to as the "base" solvents, and are present in the buffer in a final concentration of about 1% to about 80%, preferably of about 20% to 50%, for example about 40%. Suitable organic solvents for use as base solvents include, for example, propylene carbonate (also known as 1,2-propanediol cyclic carbonate) (bp=240° C.); ethylene cyclic carbonate (bp=245° C.); dimethyl phthalate (bp=282° C.); diethyl phthalate (bp=294° C.); ethylene glycol (bp=195° C.); propylene glycol (bp=185° C.); butylene glycol (bp=180° C.); dimethyl sulfoxide (bp=189° C.); methyl carbitol (bp=193° C.); and mixtures thereof. Preferred base solvents are propylene carbonate, ethylene cyclic carbonate or mixtures thereof.

Proteins are known to tightly bind to the membranes used in the present electrophoresis systems and methods (see below). In order to generate sufficient current to cause migration of proteins on the membrane, one or more conductivity enhancers are added to the base solvent.

As used herein, a "conductivity enhancer" is an organic solvent or other substance that causes an increase in current when added to a base solvent, as measured at a fixed voltage (e.g., 3.5 kV) using prewetted 1 cm by 8 cm PVDF membrane strips of about 0.1 to about 0.15 mm thickness (see Examples 1 and 2, below). The final concentration of each conductivity enhancer in the low conductivity organic solvent buffer is preferably about 0.1% to about 50%, more preferably about 5% to about 30%. Suitable conductivity enhancers include: amide compounds such as formamide, acetamide, propionamide, butyramide, toluamide, benzamide, lactamide, nicotinamide, and mixtures thereof, amide derivatives such as N-methyl formamide, N-methyl acetamide, N-methyl propionamide, and N-methyl butyramide; 2-furaldehyde; furfuryl alcohol; tetrahydrofurfuryl alcohol; salicylaldehyde; guaiacol; phenol; boric acid; fumaric acid; piperazine; and mixtures thereof. Preferred low conductivity organic solvent buffers comprise at least two conductivity enhancers. For example, the low conductivity organic solvent buffer can comprise, in addition to the base solvent, salicylaldehyde and furfuryl alcohol; a mixture of formamide, 2-furaldehyde and benzamide; a mixture of formamide and furfuryl alcohol; a mixture of formamide and tetrahydrofurfuryl alcohol or a mixture of formamide, 2-furaldehyde and boric acid.

The conductivity enhancers can, however, cause the organic solvent buffer to produce high current and excessive heat during electrophoresis. In general, heat will be generated during electrophoresis with the present buffers when the current is above 1.5 mA. Addition of one or more conductivity suppressors (also called "heat suppressors") to the base solvent/conductivity enhancer mixture can reduce heat production during electrophoresis with only a minimal effect on the migration of proteins on the membrane. Thus, the present organic solvent buffers preferably contain one or more conductivity suppressors.

As used herein, "excessive heat production" includes the generation of sufficient heat to: denature or alter the proteins being separated; boil the electrophoresis buffer or cause the buffer to entirely evaporate from the membrane; melt, char or otherwise damage the membrane or electrophoresis apparatus; or otherwise interfere with the electrophoretic separation.

As used herein, a "conductivity suppressor" is an organic solvent or other substance that causes a decrease in current when added to a base solvent which contains at least one conductivity enhancer, as measured at a fixed voltage (e.g. 3.5 kV) using prewetted 1 cm by 8 cm PVDF strips of about 0.15 mm thickness (see Examples 1 and 2, below). The final concentration of each conductivity suppressor in the low conductivity organic solvent buffer, when present, is preferably about 0.1% to about 50%, more preferably about 5% to about 30%. Suitable conductivity suppressors include: dimethyl derivatives of formamide and acetamide; 1,3-butanediol; N-methyl pyrrolidinone; sorbitol; glycerol; caprolactone; methoxyethanol; and mixtures thereof. Preferred conductivity suppressors are a mixture of 1,3-butanediol, dimethyl formamide and dimethyl acetamide; or a mixture of 1,3-butanediol and N-methyl pyrrolidinone. A particularly preferred conductivity suppressor is 1,3-butanediol.

As discussed above, too high a concentration of conductivity enhancers in the organic solvent buffer can lead to high current and excessive heat generation during electrophoresis. It is also apparent that too high a concentration of conductivity suppressors in the organic solvent buffer can lead to inadequate protein migration rates. The concentration of conductivity enhancers and conductivity suppressors in the present low conductivity organic solvent buffers must therefore be balanced, so that the overall buffer conductivity remains low, yet adequate migration of proteins is achieved without excessive heat generation. One skilled in the art can readily determine the appropriate balance of conductivity enhancers and suppressors in the present organic solvent buffers.

A convenient method for producing a low conductivity organic solvent buffer of the present invention comprises the addition of at least one conductivity enhancer to a base solvent in measured amounts, until the solution is capable of generating a current, for example, about 0.025 mA/cm$^2$ membrane (0.15 mm thickness) during electrophoresis as described in Example 2. If high current and excessive heat production is observed, one or more conductivity suppressors are added in measured amounts until heat generation is reduced to within acceptable limits. Exemplary low conductivity organic solvent buffers produced by this method are given as "Buffers A-D" in Example 1 below.

The pH of the low conductivity organic solvent buffers can be adjusted as desired, within the limits compatible with the particular buffer components. For example, the pH can be adjusted to a range of about pH 3 to about pH 10. It is understood, however, that low conductivity organic solvent buffers according to the present invention can have a pH outside of this range.

In one embodiment, organic solvent buffers of identical composition can be adjusted to different pH's. For example, a first amount of Buffer A of Example 1 can be adjusted to pH 4.5, and a second amount of Buffer A can be adjusted to pH 8.5. These first and second amounts of Buffer A can then be used sequentially in the 2-D electrophoresis of proteins, for example as described in Example 4 below.

The separation substrate used in the present invention comprises a polymeric membrane. This membrane separation substrate is analogous to the gel matrix in conventional electrophoretic methods.

Membranes for use in the present invention must be compatible with the low conductivity organic solvent buffers discussed above. For example, cellulose-derived membranes (e.g., nitrocellulose, cellulose acetate or DEAE cellulose) are destroyed by the organic solvent buffers soon after contact, rendering them useless for membrane electrophoresis. Most other types of commercially available polymeric membranes are not damaged by the present organic solvent buffers.

Membranes for use in the present invention must also have a high protein binding capacity. As used herein, a "high protein binding capacity" means the membranes bind, at room temperature, at least about 20 µg protein/cm$^2$ when the membrane thickness is about 0.15 mm. Preferably, the membranes of the invention bind, at room temperature and at a thickness of about 0.15 mm, at least about 50 µg protein/cm$^2$, and more preferably at least about 100 µg protein/cm$^2$ to about 400 µg protein/cm$^2$, for example about 150 µg protein/cm$^2$ or about 250 µg protein/cm$^2$.

Membranes for use in the present invention can be either hydrophobic or hydrophilic, and preferably have a low charge or a net neutral charge. For purposes of the present invention, it is understood that polymeric membranes designated as "neutral" are generally not devoid of charge, but either have a net neutral charge or a slight positive or negative charge. Without wishing to be bound by any theory, it is believed that proteins bind to hydrophobic polymeric membranes via hydrophobic interactions, and bind to hydrophilic membranes via ionic interactions.

Hydrophobic membranes suitable for use in the present invention include membranes comprising fluorinated polymers such as polyvinylidene difluoride (PVDF, also known in the art as polyvinylidene fluoride), polytetrafluoroethylene (PTFE), and the like; polyolefins such as polyethylene, polypropylene, polymethylpentene and the like; polystyrene or substituted polystyrenes; polysulfones such as polyethersulfone and the like; polyesters such as polyethylene terephthalate; polybutylene terephthalate and the like; polyacrylates and polycarbonates; polyurethane and vinyl polymers such as polyvinyl chloride and polyacrylonitriles; and mixtures of the above-listed polymers. Additionally, the hydrophobic membranes can comprise copolymers; e.g., of butadiene and styrene; fluorinated ethylene-propylene copolymer; and the like. Preferably, the hydrophobic membranes comprise polymeric fluorocarbons such as polyvinylidene difluoride (PVDF).

The hydrophobic membranes can also comprise modified forms of the above polymers, such as are known in the art. For example, hydrophobic polymeric membranes can be modified to contain fixed formal positive charge groups by contacting the membranes with a polyamine or a polyamidopolyamine epichlorohydrin resin, as described in U.S. Pat. No. 5,004,543 of Pluskal et al., the entire disclosure of which is herein incorporated by reference.

Hydrophilic membranes suitable for use in the present invention include membranes comprising polyamides such as nylons (e.g., nylon 66, nylon 6, nylon 610 or nylon 46); polyimides; polyesters; polyvinyl alcohols; polyvinylamines; polybenzylamides; polyvinylimidazolines; polydiallylamines; and mixtures thereof. Preferred hydrophilic membranes comprise neutral or slightly positively charged nylon polymers (e.g., Hybond™-N or Hybond™-NX blotting membranes, available from Amersham Biosciences, Piscataway, N.J.).

The charge carried by a nylon membrane is primarily determined by the type of compound added to terminate the synthetic reaction producing the nylon polymer. For example, if the termination compounds have carboxylic acid groups, the resulting nylon will be negatively charged. Likewise, if the termination compounds have amino groups, the resulting nylon will have a positive charge.

Typically, termination of the nylon synthetic reaction with amino-group containing compounds will produce a nylon polymer containing about 0.4 mole to about 2 moles amino groups per mole of nylon; membranes comprising such nylon polymers are preferred. For example, nylon membranes containing at least 0.9 mole amino end groups per mole of nylon, or at least 1.3 moles amino end groups per mole of nylon, are described in U.S. Pat. No. 5,458,782 of Hou et al., the entire disclosure of which is incorporated herein by reference. One of ordinary skill in the art can readily determine the amount of amino acid end groups per mole of nylon in a nylon membrane, for example by the methods disclosed in U.S. Pat. No. 5,458,782 of Hou et al., supra.

Membranes comprising highly positively charged nylons are known in the art, and are typically prepared by contacting a conventional nylon membrane with a solution containing a polyamine or polyamino-polyamine epichlorohydrin cation resin. Such highly positively charged nylon membranes will allow a certain amount of protein migration in the present electrophoretic methods, but generally do not produce adequate sample resolution (see Example 2 below). Therefore, highly positively charged nylon membranes are not preferred. In contrast, membranes comprising less positively charged nylons, as described in the preceding paragraph, and so-called "neutral" nylon membranes, produce good resolution of proteins by the present methods.

The polymeric membranes of the present invention typically have an average pore size of about 0.01 to about 5 microns, although membranes with larger or smaller pores can be used. Membranes with pore sizes between 0.05 and 1 micron are preferred, and membranes with pore sizes are between 0.1 and 0.5 microns are particularly preferred.

The size (i.e., length and width) of the membrane used in the present invention is generally determined by the particular separation technique to be performed. A suitable membrane size for many membrane electrophoresis methods is approximately 7.5 cm by 8 cm, although larger and smaller sizes can be used. For example, for high-throughput screening applications, the membrane can be cut into strips of approximately 1 cm by 8 cm. For applications that require extremely high resolution of the separated proteins, or for separating large numbers of proteins, the membrane can be cut to 20 cm by 20 cm or larger. One of ordinary skill in the art can readily determine an appropriate membrane size for the particular separation technique.

Membranes of the invention can be any thickness which is compatible with the separation technique to be performed. Commercially available membranes are typically about 0.10 to about 0.15 mm thick, which thickness is suitable for most electrophoretic applications; e.g., those requiring the separation of up to 15 micrograms of protein per sample. Samples containing larger quantities of proteins can also be separated. Membranes of other thicknesses, e.g., from about 0.01 mm to about 3 mm or greater are also contemplated for use in the present invention. Membranes with a thickness of about 0.05 mm to about 0.5 mm, for example about 0.1 mm to about 0.3 mm are particularly preferred.

The buffers and membranes described above can be combined with an electrophoresis apparatus to form an electrophoresis system of the invention. As used herein, an "electrophoresis apparatus" comprises at least one electrophoresis unit (often called a "gel box") for containing the buffer and membrane, and a power supply for generating an electric current in the electrophoresis unit.

Electrophoresis units are known in the art, and can be generally separated into units in which the separation substrate is oriented horizontally or vertically. The present membrane electrophoresis can be performed on either type of unit, but is preferably performed on a unit where the separation substrate is oriented horizontally (a "horizontal electrophoresis unit"). A horizontal electrophoresis unit useful in the present invention generally comprises two buffer reservoirs flanking a fixed platform on which the membrane separation substrate is placed. Electrodes are mounted in the buffer compartments, and the top of the unit is typically covered for safety purposes. The membrane must be in contact with the buffer in both buffer chambers, either directly or through a wick. The wick is typically made of filter paper. A current is produced in the electrophoresis unit by connecting a power supply to both electrodes and applying a voltage across the electrodes.

Electrophoresis units for use in the present invention can be constructed from any material which is compatible with the low conductivity organic solvent buffers described above. Generally, conventional electrophoresis units made from plastic or PlexiGlas® are not suitable for use in the present invention, as these materials are damaged by organic solvents. Electrophoresis units built of ceramics, teflon, glass or other materials resistant to organic solvents, or conventional PlexiGlas® or plastic electrophoresis units that are coated with organic solvent resistant materials (e.g., teflon or rubber), can be used.

A modified horizontal electrophoresis unit, generally designated as 100 in FIG. 1, was developed for the membrane electrophoresis system and methods. The unit comprises buffer chambers 110 and 110' located at opposite ends of the unit. Electrodes 120 and 120' are located adjacent to buffer chambers 110 and 110', respectively, so that the electrode leads 125 and 125' extend into the buffer chambers. The electrode leads, which are typically in the form of wires, can be any material capable of conducting electricity (e.g., platinum). A fixed, raised platform 130 separates the two buffer chambers, and prevents fluid communication between the chambers when they are filled with buffer.

In practice, at least one protein sample is spotted on high protein binding polymeric membrane 140, allowed to dry, and the membrane is wetted with the low conductivity organic solvent buffer. The membrane is then blotted to remove excess buffer, and placed directly on a filter paper wick 150 previously wetted with the same organic solvent buffer. The filter paper wick 150 rests on the platform 130. The membrane 140 can be coextensive in length and width with the platform 130, but usually is smaller in both length and width. In the embodiment shown in FIG. 1, the filter paper wick is longer than platform 130 so that either end of the wick extends into the buffer chambers. In a separate embodiment, the filter paper wick 150 can be replaced with two wicks, each of which overlaps with one end of membrane 140 and extends into a buffer chamber. In yet another embodiment, electrophoresis can be carried out with the membrane sandwiched between two plates without a wick or wicks. In this latter arrangement, both ends of the membrane extend into the two buffer chambers and act as wicks. In the first two embodiments discussed above, the wick or wicks draw buffer from the buffer chambers to the membrane, and help establish an electrical connection between the two buffer chambers through the membrane.

A top plate 160 is placed over, and is in direct contact with, the membrane. To prevent inadvertent electric shock during electrophoresis, a cover 170 is placed over the entire unit before voltage is applied across the electrodes. The top plate 160 and cover 170 can be made of any suitable non-electrically conductive material which is resistant to the organic solvent buffers; e.g., glass, ceramic, teflon, or PlexiGlas® coated with a material that is resistant to the organic solvent buffers. Preferably, top plate 160 and cover 170 are made of teflon or glass.

Figure 2:
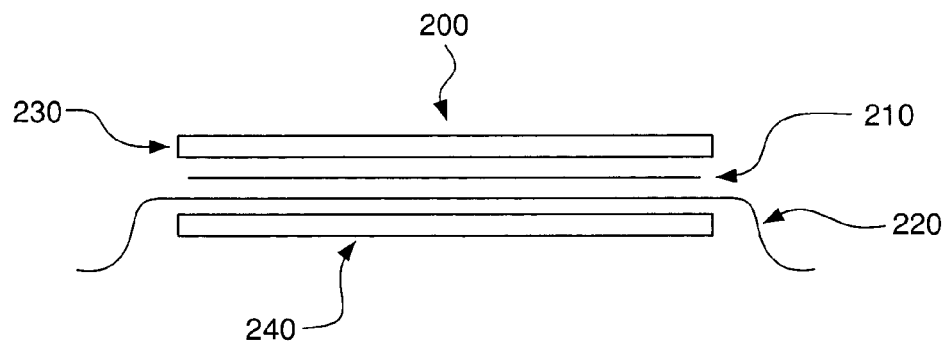
FIG. 2 is a side view of a "sandwich unit" containing a membrane and wick for use in horizontal electrophoresis units of the invention.

FIG. 2 shows an alternative arrangement for the membrane separation substrate and filter paper wick. In this arrangement, a membrane 210 and a filter paper wick 220 are sandwiched between top plate 230 and bottom plate 240 to form a "sandwich unit" generally designated as 200. The plates 230 and 240 are generally coextensive in length and width. The membrane 210 can be of variable size, but preferably has dimensions which are less than that of the plates 230 and 240. In the embodiment shown, the filter paper wick 220 has a greater length than the plates 230 and 240 so that wick material protrudes from the plates at either of the sandwich unit. The plates 230 and 240 can be made of any suitable non-electrically conductive material which is resistant to the organic solvent buffers; e.g., glass, ceramic, teflon, or PlexiGlas® coated with a material that is resistant to the organic solvent buffers. Preferably, the plates 230 and 240 are made of teflon or glass.

Referring again to FIG. 1, the sandwich unit 200 from FIG. 2 can be placed on platform 130 so that the ends of the filter paper wick extend into buffer chambers 110 and 110'.

Figure 3:
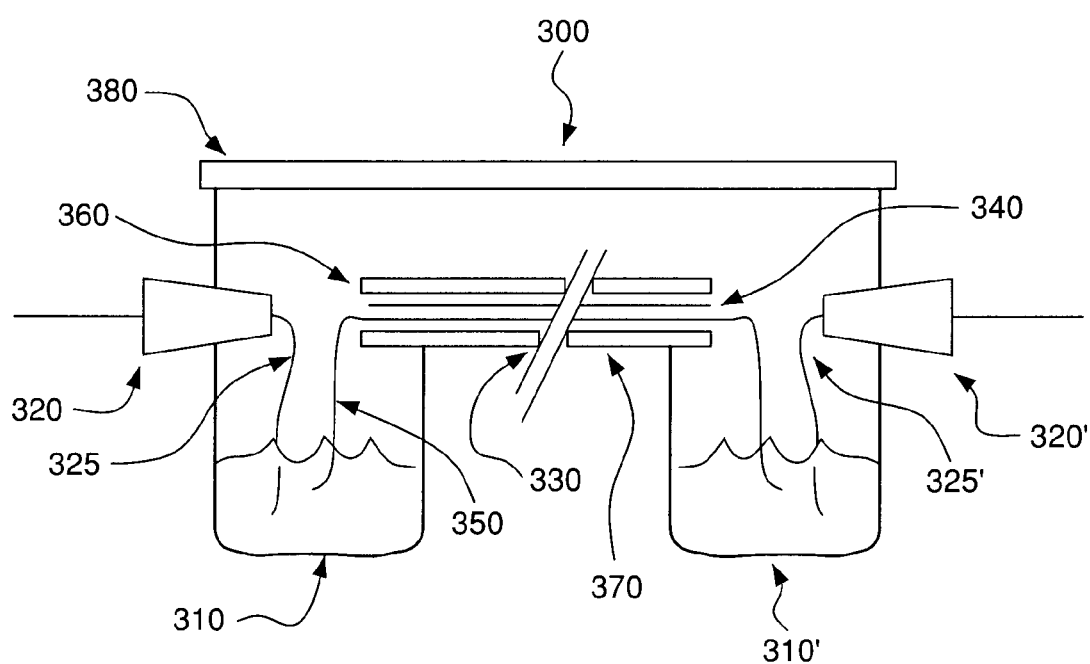
FIG. 3 is a side cutaway view of a variable length horizontal electrophoresis unit of the invention, showing two independent buffer chambers and a variable length sandwich unit.

Another embodiment of the electrophoresis unit is shown generally as 300 in FIG. 3. This unit comprises two independent buffer chambers 310 and 310'. Electrodes 320 and 320' are located adjacent to the buffer chambers, and have electrode leads 325 and 325' extending into the buffer chambers. There is no fixed platform between the buffer chambers; rather, a variable length sandwich unit 330 is used as the platform during electrophoretic separation. The sandwich unit 330 comprises a membrane 340 and filter paper wick 350 held between a top plate 360 and bottom plate 370. Because there is no fixed platform connecting the buffer chambers, the independent buffer chambers 310 and 310' can be spaced as appropriate to accommodate sandwich units of varying lengths. In practice, sandwich unit 330 is placed across appropriately spaced independent buffer chambers 310 and 310', such that either end of the filter paper wick is in contact with the buffer solution in the buffer chambers. A cover 380 is placed over the entire unit before voltage is applied across the electrodes. The plates 360 and 370 and cover 380 can be made of any suitable non-electrically conductive material which is resistant to the organic solvent buffers; e.g., glass, ceramic, teflon, or Plexi-Glas® coated with a material that is resistant to the organic solvent buffers. Preferably, plates 360 and 370 and cover 380 are made of teflon or glass.

Any power supply capable of generating a voltage adequate to achieve the desired electric current can be used in the membrane electrophoresis systems and methods. Typical commercially available power supplies can generate a voltage of 3 to 4 kV, which is suitable for most membrane electrophoresis separations. Power supplies that can generate higher voltage, for example up to 75 kV, are also commercially available. One of ordinary skill in the art can readily obtain or construct power supplies capable of generating the required voltage for the present system and methods.

Membrane electrophoresis methods according to the present invention are generally performed as follows. Specific membrane electrophoresis protocols are described in the working examples below.

A polymeric membrane as described above is cut to the desired size for the separation technique to be performed. Generally, the membrane has no wells, indentations, or other surface features designed to hold the sample to be loaded. The samples comprising proteins to be separated are then loaded onto the membrane by any suitable technique; e.g., by "spotting" the samples onto the membrane with a transfer pipette or micropipette. For example, when loading protein samples onto hydrophobic membranes (e.g., PVDF), a wetting agent such as ε-caprolactone or dimethylformamide is added to the sample prior to application. Preferably, the sample is allowed to dry on the membrane at room temperature. As discussed below, the proteins can move towards either electrode along the axis of the applied electric current. Thus, the samples are generally spotted on the membrane approximately midway between the two electrodes. Samples can also be spotted on other areas of the membrane to achieve specific separation. It is understood that multiple samples can be loaded onto a single membrane.

Protein samples can be obtained from any source, by methods within the skill in the art. For example, protein samples can be obtained from unicellular organisms or multicellular organisms. In one embodiment, protein samples are obtained directly from multicellular organisms (e.g., humans) by taking a sample of tissue, cells, blood, serum, or other biological material from the organism. Protein samples can also be obtained by removing aliquots from a preparation comprising natural or synthetic proteins; for example, from a serum or blood sample, or a pharmaceutical formulation.

The membrane is then wetted in the low conductivity organic solvent buffer to be used for the electrophoretic separation. It is generally desirable to remove excess buffer from the membrane; e.g., by blotting with a paper towel. A filter paper wick previously wetted with the same organic solvent buffer is placed in position on the electrophoresis unit platform (or bottom glass plate, if a sandwich unit is being employed). The membrane is placed in position on the filter paper wick, and both buffer chambers are filled with electrophoresis buffer. A top glass plate is placed on top of the membrane containing the protein samples or mixtures. The electrophoresis unit is covered with a cover plate and the power supply is connected to the electrodes. With a power supply unit that generates high voltages, for example 75 kV, multiple electrophoresis units (e.g., 4 or more units) may be connected to a single power supply. The power supply is then switched on and the voltage output adjusted to achieve the desired current through the electrophoresis unit or units. Separation of the proteins in the sample begins upon application of electric current to the electrophoresis unit or units.

Figure 9:
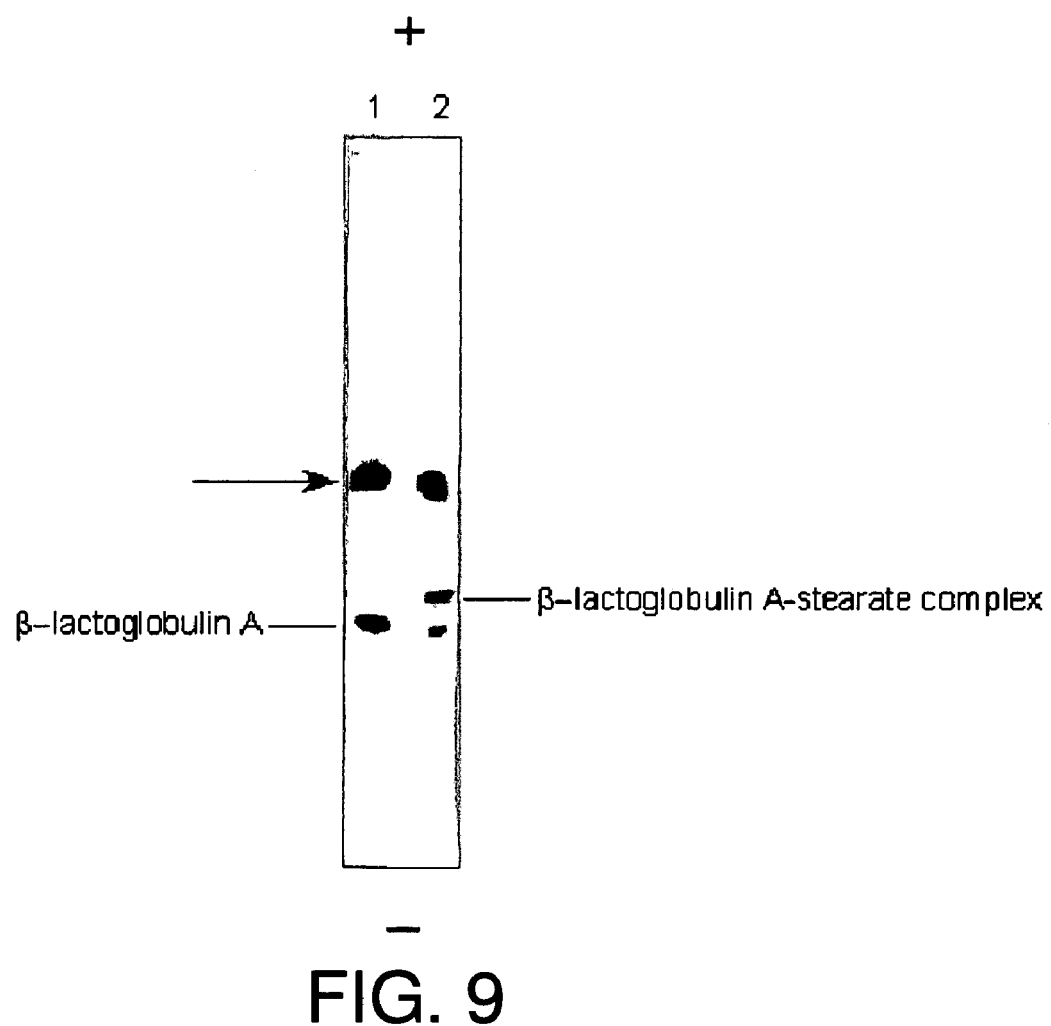
FIG. 9 shows the detection of a β-lactoglobulin A/stearate complex after electrophoresis of the complex on a PVDF membrane according to the invention. The orientation of the membranes with respect to the positive and negative electrodes during electrophoresis is indicated by a "+" and "−". The arrow represents the origin.

It is understood that the proteins migrate in a direction parallel to the membrane surface, as opposed to migrating in a direction which is perpendicular to the membrane surface. Without wishing to be bound by any theory, the protein in the samples are believed to migrate along the surface of the membrane during electrophoresis, and not through the membrane. See, for example, FIG. 9 below, in which indentations were inadvertently created in the membrane surface with the micropipet tip used to load the samples in both lanes. The indentations trapped some of the sample at the origin in each lane.

Further evidence that the protein samples migrate on the surface of the protein binding membranes during the present membrane electrophoresis methods can be seen in Examples 10a and 10b. In Example 10a, a protein binding membrane on which proteins were separated according to the present methods was cut in cross-section and subjected to confocal microscopy. The protein in the samples was seen to be associated only on the surface of the membrane. Example 10b shows that protein samples are lost from the protein binding membrane, or become more diffuse, during electrophoresis when the entire sample side of the membrane is in direct contact with the filter paper wick.

Again without wishing to be bound by any theory, separation of proteins by the present membrane electrophoresis methods apparently involves the weakening of the strong surface interactions between proteins in the sample and the protein binding membrane by the organic solvent buffers. This allows the proteins to migrate across the surface of the protein binding membrane when subjected to an electric current.

The amount of protein per sample that can be loaded onto the membrane will vary, and is influenced by factors such as the purity of the sample, the purpose of the electrophoresis technique, and the practical detection limit of the visualization or staining technique to be used. Generally, the amount of protein per sample can range from about 0.025 to about 15 micrograms. One of ordinary skill in the art can readily determine an appropriate amount of protein to be loaded in each sample.

Due to the organic character of the low conductivity electrophoresis buffer, samples comprising hydrophobic or low molecular weight (e.g., $M_r \leq 10,000$) proteins, as well as samples comprising hydrophilic proteins, can be readily separated by the present methods.

Prior to loading, the samples can be mixed with substances which aid in the placement and retention of the samples on the membrane. For example, the sample can be mixed with an equal volume of an organic solvent such as caprolactone or dimethyl formamide before spotting onto a hydrophobic membrane.

The sample can also be mixed with substances which aid in visualizing the extent of protein migration during the electrophoresis. Generally, such substances are dyes which migrate slightly before or along with the fastest migrating protein, although slower migrating substances can also be used. For example, the protein sample can be mixed with bromophenol blue, which typically migrates ahead of the fastest migrating protein. Fluorescent dyes such as acridine orange can also be used.

One or more proteins in the sample can also be labeled with a detection agent prior to loading onto the membrane. Suitable detection agents include colored dyes; fluorescent dyes; chemiluminescent labels; biotinylated labels, radioactive labels; affinity labels; enzyme labels; protein-specific antibodies; fluorescent antibodies and the like. Suitable fluorescent dyes include CyDye 2, 3 or 5 DIGE fluors available from Amersham Biosciences. In one embodiment, several samples, each containing a different fluorescently labeled protein, can be loaded onto the same membrane and electrophoresed. Alternatively, a single sample can comprise proteins labeled with different detection agents.

Other manipulations can also be performed on the samples prior to loading onto the membrane, including boiling or denaturing, mixing of the samples with suspected ligands, immunoprecipitation, and the like.

Depending on the size of the membrane, electrophoresis is generally performed at about 1 to about 4 kV, although voltages as low as about 0.1 kV and as high as about 30 kV can be used. Preferably, the voltage used is about 2 kV to about 4 kV. The voltage is applied to the electrophoresis unit for an amount of time sufficient to separate the proteins which have been loaded onto the membrane. The time required for separating proteins varies, and is influenced by factors such as the voltage applied, the amount and complexity of the protein sample, and the goal of the particular separation application. Generally, the separation time can be shortened with the use of higher voltages (e.g., from about 10 to about 20 kV). One of ordinary skill in the art can readily determine an appropriate separation time for a given set of membrane electrophoresis conditions.

The current generated in the membrane electrophoresis methods should be in the range of about 0.0001 mA/cm$^2$ membrane to about 0.2 mA/cm$^2$ membrane, preferably 0.0005 mA/cm$^2$ membrane to about 0.05 mA/cm$^2$ membrane, more preferably about 0.001 mA/cm$^2$ membrane to about 0.025 mA/cm$^2$ membrane. When using a membrane of approximately 60 cm$^2$ (i.e., about 7.5 by 8 cm), currents of about 0.005 mA to about 5 mA, preferably about 0.01 mA to about 1.5 mA, more preferably about 0.03 mA to about 1.2 mA, particularly preferably about 0.05 to 1.0 mA, are generated. No significant heat is produced during membrane electrophoresis at currents below 1.5 mA.

Without wishing to be bound by any theory, migration of proteins on the membrane appears to be related to their isoelectric point ("pI"). For example, when the pH of the organic solvent buffer is equal to the pI of a protein molecule in the sample, that protein has a neutral charge and no migration of the protein is observed. However, if the pH of the organic solvent buffer is above the isoelectric point of a protein in the sample, that protein is positively charged and it migrates to the cathode. Likewise, proteins that are negatively charged in the buffer migrate towards the anode. The greater the difference between the pI of a protein and the pH of the buffer, the faster the migration of the protein. Again without wishing to be bound by any theory, the molecular weight of the proteins does not appear to substantially influence migration during membrane electrophoresis.

In general, proteins within 5 pI units of the pH of the organic buffer can be separated. For example, as shown in Example 2 below, an organic solvent buffer having a pH of 4.5 permits the separation of proteins with pI's ranging from about 1 to 9.6. Therefore, an organic solvent buffer with a pH of 8.5 can be expected to separate proteins with pI's of about 3.5 to as high as 12 or 13. It is understood, however, that proteins for which the difference between the pI and the buffer pH is greater than 5 units can also be separated by the present methods.

As used herein, the axis of protein migration along the membrane defines a "dimension." The axis of protein migration can be changed either by applying the electric current in a different direction relative to the orientation of the membrane, or by re-orienting the membrane in the original electric current. In 1-D electrophoretic techniques, the axis of protein migration is not changed. For 2-D techniques, the axis of protein migration is changed, for example, by turning the membrane in the electrophoresis unit.

Thus, in 1-D membrane electrophoresis techniques, proteins are separated only in a single dimension according to their isoelectric points, as influenced by the pH of the electrophoresis buffer. 1-D membrane electrophoresis techniques can be used in a wide variety of applications. In particular, 1-D membrane electrophoresis techniques are useful for the rapid analysis of the protein composition of a sample, or for the rapid analysis of therapeutic protein preparations, vaccines or blood samples for the presence of contaminants and degradation products. An exemplary 1-D analytic membrane electrophoresis technique is given in Example 9 below.

In 2-D membrane electrophoresis techniques, proteins are separated in a first dimension according to their isoelectric points as influenced by the pH of a first electrophoresis buffer, as in 1-D membrane electrophoresis. However, separation of the proteins in a second dimension is performed in a second buffer that has a pH value which is different from the first buffer. In practice, the membrane is typically removed from the electrophoresis unit after separation of the proteins in the first dimension, and is equilibrated in the second buffer. Preferably, the membrane is washed at least once; e.g., one to four times, in water to remove the first buffer before being equilibrated in the second buffer. For example, a suitable washing step can comprise placing the membrane in a tray of water with shaking for 20 minutes, with 3 to 4 changes of water within that time period.

If a wick is used, the first wick is usually discarded, and a second wick is equilibrated in the second buffer. The first buffer is also removed from the electrophoresis unit, and the buffer chambers are filled with the second buffer. The equilibrated membrane is then placed in the electrophoresis unit in a different orientation, and the electric current is re-applied. The different pH of the second buffer causes the proteins separated in the first dimension to become differently charged. Upon application of the electric current, the proteins migrate in the second dimension based on the pH of the second buffer. As can be seen in Example 4, high resolution separation of a large number of proteins can be achieved with the 2-D membrane electrophoresis method.

It is understood that the first and second buffers for use in 2-D membrane electrophoresis can have the same composition, but a different pH. For example, the pH of the first and second buffers can be adjusted as described in Example 1 below. Alternatively, the first and second buffers can have a different composition and a different pH.

The membrane electrophoresis methods of the invention appear to be similar to conventional isoelectric focusing (IEF) techniques in terms of protein separation based on their isoelectric points. However, the present membrane electrophoresis methods have several advantages over conventional IEF procedures. First, conventional IEF involves the separation of charged protein molecules in a gel matrix with a preformed pH gradient (e.g., by ampholytes or immobilized pH strips). The preformed pH gradients are expensive and time-consuming to prepare. Also, proteins with pI's less than 3 or above 10 cannot easily be separated by conventional IEF due to the difficulty in obtaining suitable ampholyte gradients or preformed IEF strips. In contrast, no preformed pH gradients are required for the present membrane electrophoresis methods, and proteins with pI's as low as 1 and as high as about 12 or 13 can be readily separated using membrane electrophoresis.

Secondly, conventional IEF gels typically contain a high concentration of urea (e.g., 9M) and other nonionic detergents which eliminate protein-binding interactions and enzymatic activities. Also, the gels used for the second dimension separation by 2-D PAGE separates proteins by molecular weight and typically contain ionic detergents such as SDS. In contrast, the present 2-D membrane electrophoresis can use water-miscible organic solvents in the absence of urea or detergents, thus preserving vital protein-binding interactions and biological activities.

Thirdly, separation of hydrophobic proteins is generally prohibited in conventional IEF procedures due to the inability of such proteins to be solubilized in the aqueous buffers. Because organic solvent buffers are used in the present 2-D membrane electrophoresis, both hydrophobic and hydrophilic proteins can be readily separated.

Finally, conventional IEF procedures take 1 to 2 days to complete, whereas a typical 2-D membrane electrophoresis can be completed in 30 minutes or less. The speed of the present 2-D membrane electrophoresis methods, in particular when coupled with the attachment of multiple electrophoresis units to a single power supply, allows the analysis of exceedingly high numbers of protein samples in a greatly reduced time-frame.

2-D membrane electrophoresis techniques are useful for analyzing protein samples taken at different time points from an organism or part of an organism (e.g., from cell, tissue or other biological samples obtained from an organism). In particular 2-D membrane electrophoresis is useful for analyzing protein samples obtained from an organism or part of an organism (e.g., from cell, tissue or other biological samples obtained from an organism) which are obtained during different developmental stages. For example, protein samples can be obtained from a single organism throughout embryogenesis.

Any alteration in protein expression during different developmental stages will typically manifest in the appearance, disappearance or mobility shift of protein spots on the protein binding membrane after separation by the present methods. The appearance, disappearance or mobility shift of protein spots can be used in the detection of the differentially expressed proteins. The nature of the differentially expressed proteins can be identified by mass spectrometry, immunodetection, or other suitable techniques within the skill in the art.

When analyzing protein samples obtained from different time points by 2-D membrane electrophoresis, it is preferable to use larger protein-binding membranes, for example 20 cm×20 cm, as multiple samples can be applied to different regions of the membrane and run simultaneously.

The present membrane electrophoresis methods also comprise "pulsed-field" electrophoresis techniques, such as are known in the art.

After the proteins have been separated by membrane electrophoresis, they can be detected on the membrane with standard staining or visualization techniques. Such techniques include calorimetric protein detection methods (e.g.; employing ponceau S, Coomassie blue, or amido black); colloidal gold staining; silver staining coupled with silver enhancement; immunostaining, chemiluminescent detection, fluorescent imaging; radioimaging, and the like, as are known in the art. Staining or visualization techniques which are highly sensitive are preferred. For example, colloidal gold staining can detect approximately 1 to 2 nanograms (ng) of protein on a membrane, and silver staining coupled with silver enhancement can detect approximately 0.5 ng protein on a membrane. However, the colloidal gold staining takes up to 2 hours to complete and does not stain proteins separated on all types of membranes with equal sensitivity (Pluskal et al., *Biotechniques* 4:272-283, 1986). Silver staining coupled with silver enhancement is also very time consuming and difficult to perform.

A novel and highly sensitive protein staining method using the Reactive Brown fabric dye has been developed. The Reactive Brown staining method is particularly suited to detecting proteins separated by membrane electrophoresis, and is the subject of the commonly owned U.S. Provisional Patent Application Ser. No. 60/409,857, titled "Method of Visualizing Proteins Bound to Protein Binding Membranes," filed on Sep. 11, 2002 and incorporated herein by reference in its entirety. This method can rapidly detect proteins separated by membrane electrophoresis down to about 1 ng, with approximately equal sensitivity on the various types of polymeric membranes described above. At this level of sensitivity, it is possible to resolve several hundred protein spots separated on a 7.5 cm×8 cm membrane according to the present methods.

Figure 12A:
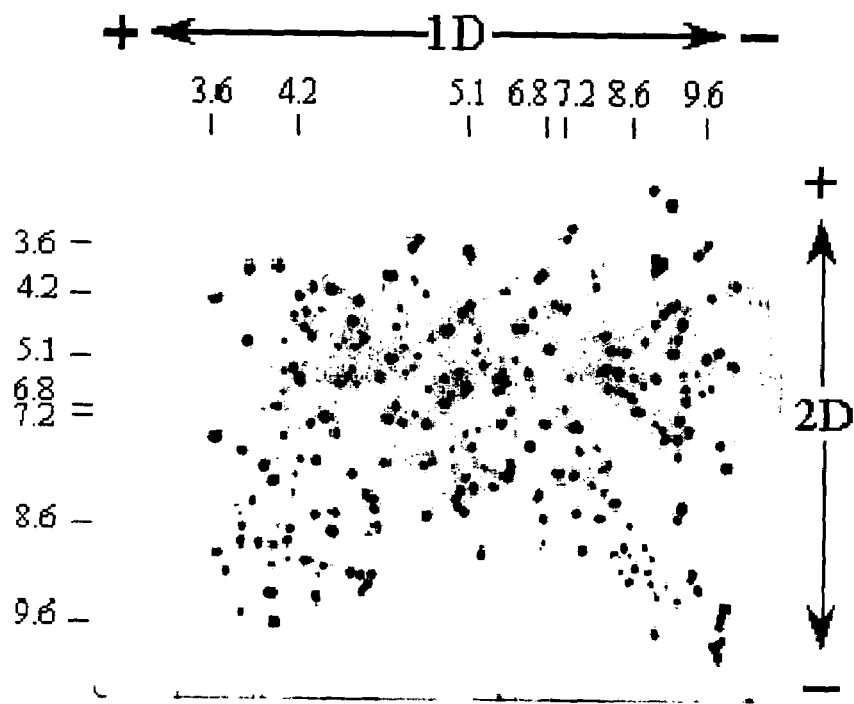
FIGS. 12A and 12B show, respectively, 2D membrane electrophoreses of the hydrophilic and hydrophobic protein fractions of human serum, separated on PVDF membranes and silver stained.

In one embodiment, the membrane electrophoresis can be conducted under non-denaturing conditions (e.g., in the absence of urea or SDS). Under non-denaturing conditions, protein-binding interactions are retained during and after electrophoresis. For example, the inventors have analyzed the protein composition of four of the protein spots shown in FIG. 12A by mass spectrometry, and have found that each of the four spots contains at least fifteen different proteins. Other methods within the skill in the art can be used to identify proteins separated by the present methods under non-denaturing conditions, including sequencing or immunodetection with protein-specific antibodies (e.g., Western analysis).

There are two different types of protein-binding interactions which can be detected by the present methods. The first is an endogenous protein-binding interaction, which is a protein-binding interaction among proteins originally present in a sample such as a cell extract. The second is an induced protein-binding interaction, which is a protein-binding interaction among a protein originally present in a sample and a protein which has been added to the sample after the sample has been obtained. For example, induced protein-binding interactions can occur upon the addition of protein-specific antibodies to a sample. The added antibodies can bind to proteins originally in the sample.

An endogenous or induced protein-binding interaction can cause a mobility shift of a protein which has been bound by another protein. Mobility shifts can be easily detected, and thus the proteins added to the sample do not have to be labeled. In one embodiment, however, proteins added to a sample can be labeled. Preferably, a protein added to the sample which causes an induced protein-binding interaction is an antibody.

Without wishing to be bound by any theory, mobility shifts of proteins in a sample which are bound to another protein are believed to be due to a change in the isoelectric point of the bound proteins as compared to the same unbound proteins in a sample.

In one embodiment, an antibody to be added to a sample can be labeled; e.g., by colored dyes, fluorescent dyes, chemiluminescent labels, biotinylated labels, radioactive labels, affinity labels, or enzymatic labels. Mobility shifts of proteins in the sample bound by the labeled antibodies can then be detected by virtue of the label, using techniques within the skill in the art. The antibody/protein complexes can also be detected on the protein binding membrane after electrophoresis with secondary antibodies.

In another embodiment, a protein-specific ligand can be mixed with the sample before membrane electrophoresis. The protein-specific ligand can either be unlabeled, or can be labeled as described above for antibodies. The proteins in the sample that interact with the added ligand can be detected by mobility shifts as described above, or by detecting the label.

Proteins electrophoresed with the present methods under non-denaturing conditions can also retain enzymatic activities. The separated proteins or protein complexes retaining the enzymatic activity of interest can be detected by any suitable method, for example by zymographic analysis directly on membrane. Zymographic analysis can be carried out, for example, with calorimetric or fluorogenic substrates as described in Example 8 below.

Membrane electrophoresis under non-denaturing conditions also provides a simple method for identification of protein partners in the protein-protein complexes. The nature of the protein partners can be determined by using protein-specific antibodies, enzymatic analysis, mass spectrometric analysis, protein sequencing and the like, according to procedures within the skill in the art.

The invention will now be illustrated by the following non-limiting examples.

EXAMPLE 1

Low Conductivity Organic Solvent Buffers for Membrane Electrophoresis

Low conductivity organic solvent buffers according to the invention were formulated as follows:

Buffer A—The conductivity enhancers salicylaldehyde (5 ml) and furfuryl alcohol (3 ml) were added to the base solvent ethylene cyclic carbonate (7 ml). It is necessary to melt ethylene cyclic carbonate prior to use. Electrophoresis of sample proteins at 3.5 kV on 1 cm by 8 cm strips as in Example 2 quickly produced a current over 1.5 mA and generated excessive heat. The addition of a mixture of conductivity suppressors 1,3-butanediol, dimethyl formamide and dimethyl acetamide reduced the current to 0.1 mA and eliminated the heat generation with minimal reduction in protein migration rates. The final formulation of Buffer A was:
  28% ethylene cyclic carbonate
  20% salicylaldehyde
  12% furfuryl alcohol
  8% 1,3-butanediol
  16% dimethylformamide
  16% dimethylacetamide The pH of Buffer A was adjusted to 4.5 with formic acid, although pH's in a range of about 3 to about 6 can be achieved by varying the amount of formic acid added. In addition, the pH of Buffer A can be adjusted in the range of about 6 to about 10 by adding 0.5 M piperazine dissolved in furfuryl alcohol.

Buffer B—The conductivity enhancers formamide (3 ml), and furfuryl alcohol (3 ml) were added to the base solvent propylene carbonate (11 ml). Electrophoresis of sample proteins at 3.5 kV on 1 cm by 8 cm strips as in Example 2 produced a current of 2.0 mA and generated excessive heat. The addition of a mixture of the conductivity suppressors 1,3-butanediol and N-methyl pyrrolidinone reduced the current to 0.4 mA and eliminated the heat generation with only a minimal effect on protein migration. The final formulation of Buffer B was:
  44% propylene carbonate
  12% formamide
  12% furfuryl alcohol
  16% 1,3-butanediol
  16% N-methyl pyrrolidinone The pH of the buffer was brought to 8.5 with 0.5 M piperazine dissolved in propylene carbonate, although pH's in the range of about 6 to about 10 can be achieved by varying the amount piperazine added. The pH of Buffer B can be made acidic by adjusting the pH with formic acid. An effective pH range of 3 to 6 can be obtained for Buffer B with this adjustment.

The conductivity enhancer furfuryl alcohol can be replaced by tetrahydrofurfuryl alcohol to produce Buffer C below.
  36% propylene carbonate
  12% formamide
  20% tetrahydrofurfuryl alcohol
  16% 1,3-butanediol
  16% N-methyl pyrrolidinone The pH of the buffer was brought to 8.5 with 0.5 M piperazine dissolved in propylene carbonate, although pH's in the range of about 6 to about 10 can be achieved by varying the amount piperazine added. The pH of Buffer C can be made acidic by adjusting the pH with formic acid. An effective pH range of 3 to 6 can be obtained for Buffer C with this adjustment.

The conductivity enhancer furfuyl alcohol can also be replaced by 2-furaldehyde to produce Buffer D below.
  44% propylene carbonate
  12% formamide
  12% 2-furaldehyde
  16% 1,3-butanediol
  16% N-methyl pyrrolidinone The pH of the buffer was brought to 8.5 with 0.5 M piperazine dissolved in propylene carbonate, although pH's in the range of about 6 to about 10 can be achieved by varying the amount piperazine added. The pH of Buffer D can be made acidic by adjusting the pH with formic acid. An effective pH range of 3 to 6 can be obtained for Buffer D with this adjustment.

EXAMPLE 2

Evaluation of Membranes for Membrane Electrophoresis

Determination of Membrane Compatibility with the Buffers—The following polymeric membranes were tested for their compatibility with Buffer A or Buffer B from Example 1: polyvinylidene difluoride (PVDF), nitrocellulose, supported nitrocellulose, cellulose acetate, DEAE-cellulose, Hybond™-N, Hybond™-NX (both are neutral nylon membranes, but as indicated earlier, they may be slightly charged), Hybond™-XL, and Hybond™-N$^+$ (both are modified and highly positively charged nylon membranes). Each membrane was cut into 1 cm×8 cm strips and wetted with the either Buffer A or Buffer B. Of the membranes examined, the cellulose derived membranes (e.g. nitrocellulose, cellulose acetate and DEAE cellulose) were completely destroyed by the buffers soon after contact, rendering them useless for membrane electrophoresis. The remaining membranes were resistant to the organic solvents in the buffers, and were tested further for their suitability for use in membrane electrophoresis.

Preparation of Protein Sample for Separation—A protein sample was obtained from the dry body parts of the German cockroach *Blatella germanica* as follows. Colonies of *B. germanica* are maintained in 120-gallon plastic containers. Dry body parts of the dead cockroaches were collected from the bottom of the 120-gallon container and homogenized in phosphate buffered saline (PBS), pH 7.4 with a mortar and pestle to form a slurry (approximately 1 g of dry body parts/5 ml PBS). The slurry was then centrifuged at 13,000×g for 30 min. The supernatant was dialyzed against water to remove low molecular weight impurities. The protein content of the dialyzed sample was determined by standard methods, and the sample was aliquotted and stored at −20° C.

Electrophoresis of *B. germanica* Proteins—Two microliters of the dialyzed sample of *B. germanica* proteins prepared above (1.5 µg total protein) was mixed with an equal volume of caprolactone and spotted at the center of the various 1 cm×8 cm membrane strips. The addition of caprolactone facilitates the binding of the protein extract onto the hydrophobic PVDF membrane. A 1 cm by 8 cm strip of Whatman 3 mm filter paper was used as a control. The membranes and Whatman 3 mm filter paper control strip were each soaked briefly in Buffer A and blotted to remove any excess solvent. The membranes and control strip were placed on top of a long filter paper wick, and the wick and membranes were sandwiched in between two glass plates. The wick was longer than the membranes and the glass plates, and the ends of the wick protruded from the glass plates. This "sandwich unit" was positioned on the raised platform of a horizontal electrophoresis unit much like the one shown in FIG. 1, so that the ends of the wick extended into filled buffer compartments. A protective glass cover was placed over the top of the unit, and a power supply was connected to the platinum electrodes of the electrophoresis unit. A voltage of 3.5 kV was then applied to the unit for 5 minutes.

The membranes and control strip were removed from the electrophoresis unit and stained with Reactive Brown dye according to the method disclosed in the commonly owned U.S. Provisional Patent Application Ser. No. 60/409,857, supra, titled "Method of Visualizing Proteins Bound to Protein-Binding Membranes," filed on Sep. 11, 2002. The results of the electrophoretic separation are shown in FIG. 4.

Figure 4:
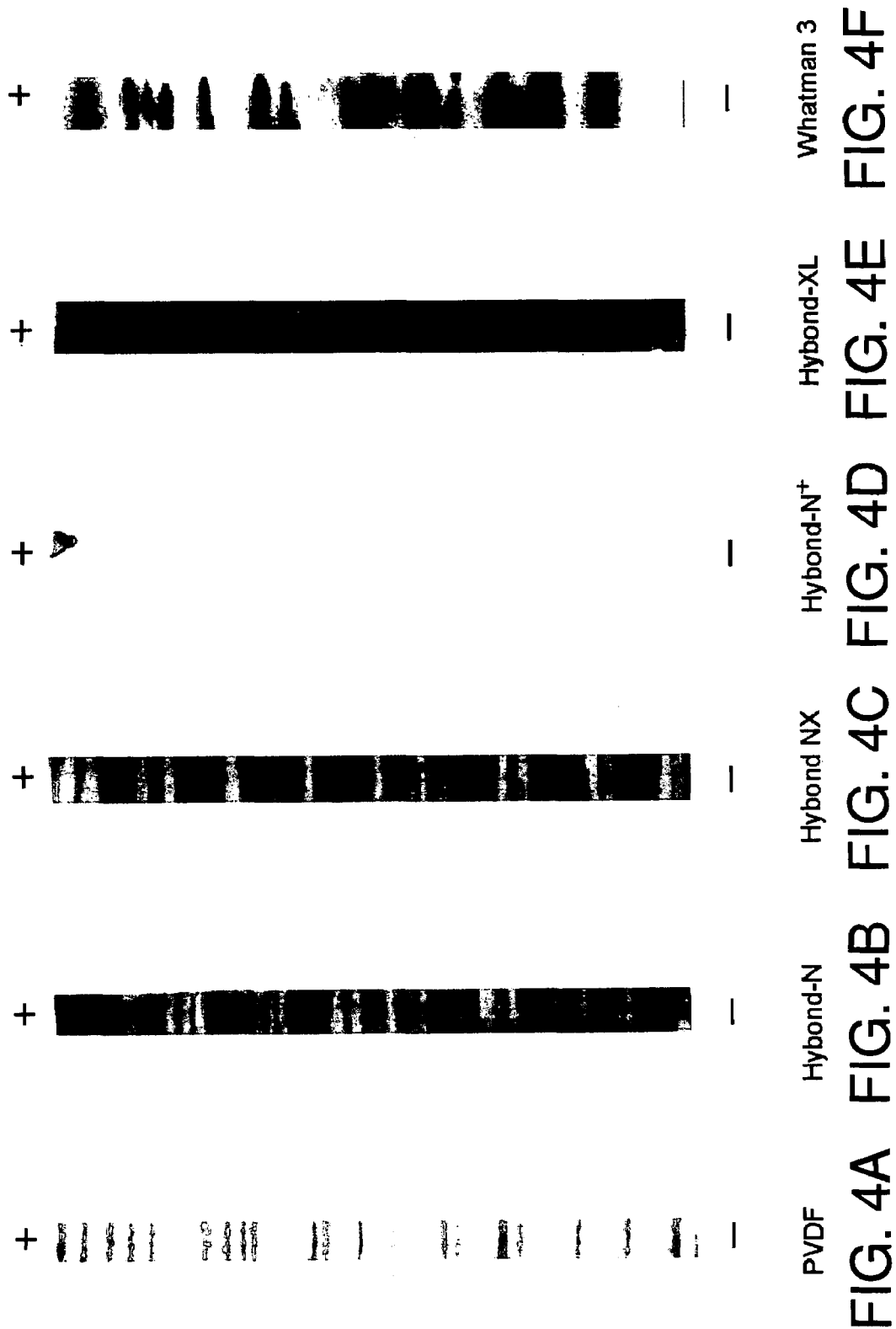
FIG. 4 shows a Reactive Brown stain of *B. germanica* proteins electrophoresed on various membrane strips. A: PVDF membrane; B: neutral nylon membrane (Hybond™-N); C: neutral nylon membrane (Hybond™-NX); D: charged nylon membrane (Hybond™-N+); E: charged nylon membrane (Hybond™-XL); F: Whatman 3 mm filter paper control strip. The orientation of the strips with respect to the positive and negative electrodes during electrophoresis is indicated by a "+" and "−".

As can be seen from the figure, the best protein separation was achieved with the PVDF membrane (FIG. 4, lane A). Both neutrally charged nylon membranes (Hybond™-N and Hybond™-NX) showed good protein separation (FIG. 4, lanes B and C). However, the protein sample applied onto either Hybond™-N+ or Hybond™-XL (both are highly positively charged nylon membranes) had a greatly reduced migration rate and resolution was poor compared to the resolution seen on the neutral nylon or PVDF membranes (FIG. 4, lanes D and E). The filter paper control strip showed poor resolution and excessive band diffusion (FIG. 4, lane F). These results suggest that for polymeric membranes to be useful for membrane electrophoresis, the membranes are preferably either hydrophobic (e.g. PVDF) or hydrophilic with little or no net charge (e.g. Hybond™-N and Hybond™-NX). Filter paper is clearly unsuitable for use in the present methods.

Similar results were obtained for electrophoresis of the *B. germanica* proteins in Buffer B, using the same conditions and arrangement of the electrophoresis unit. Membrane electrophoreses of *B. germanica* proteins were also performed using different wick arrangements (i.e., two wicks instead of one; direct communication of the membranes with the buffer chambers without a wick), and arrangements in which a top plate was not placed directly over the membranes. These arrangements produced some heat generation, localized drying of the membranes, and buffer condensation on the glass cover plate. However, satisfactory protein separation was obtained with each arrangement.

EXAMPLE 3

One-Dimensional Membrane Electrophoresis

Figure 5:
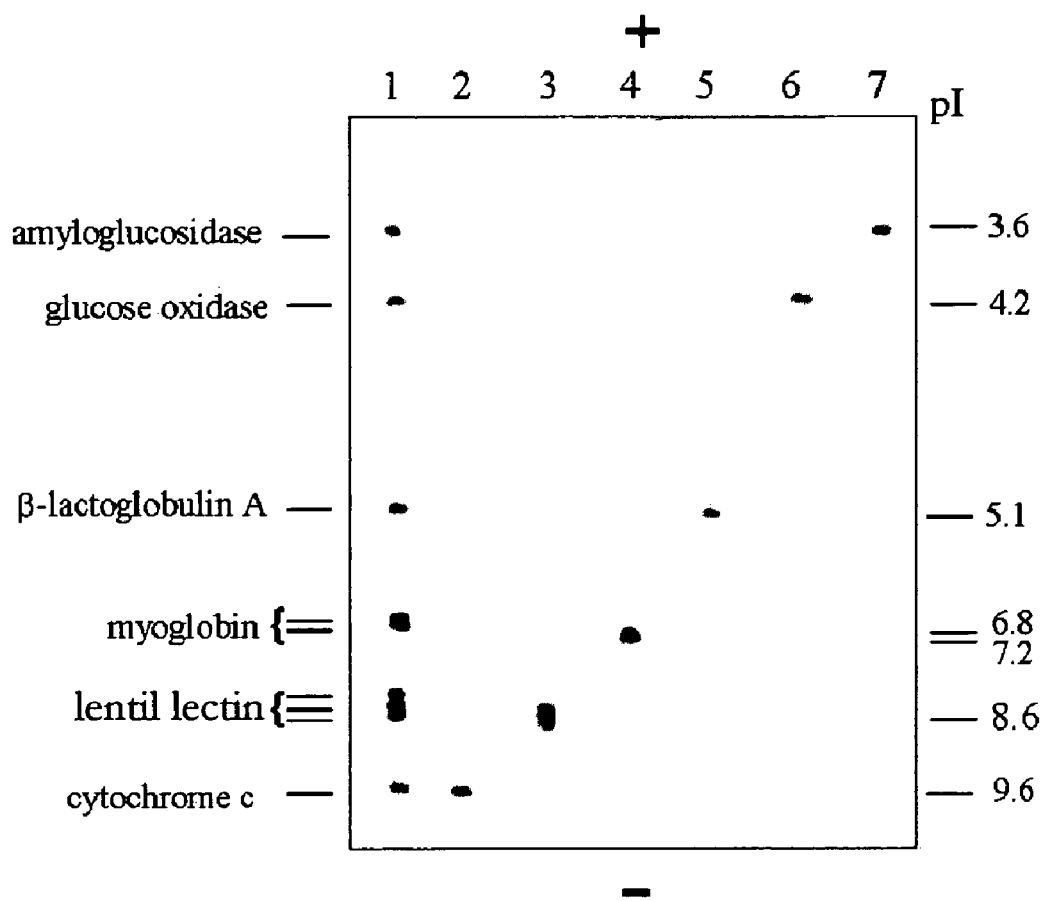
FIG. 5 is a Reactive Brown stain of six proteins electrophoresed on a PVDF membrane, showing separation of the proteins by isoelectric point ("pI"). Lane 1: mixture of amyloglucosidase (pI 3.6), glucose oxidase (pI 4.2), β-lactoglobulin A (pI 5.1), myoglobin (pI 6.8; 7.2), lentil lectin (pI 8.2; 8.6; 8.8) and cytochrome C (pI 9.6); Lane 2: cytochrome C; Lane 3: lentil lectin; Lane 4: myoglobin; Lane 5: β-lactoglobulin A; Lane 6: glucose oxidase; Lane 7: amyloglucosidase. The orientation of the membrane with respect to the positive and negative electrodes during electrophoresis is indicated by a "+" and "−".

Six proteins having isoelectric points ranging from 3.6 to 9.6 were electrophoresed on a 7.5 cm by 8 cm PVDF membrane as in Example 2, in Buffer A at 3.5 kV for five minutes. After electrophoresis, the proteins were stained with Reactive Brown as in Example 2. The six proteins were: amyloglucosidase (pI 3.6); glucose oxidase (pI 4.2); β-lactoglobulin A (pI 5.1); myoglobin (pI 6.8 and 7.2); lentil lectin (pI 8.2, 8.6 and 8.8) and cytochrome C (pI 9.6). As shown in FIG. 5, the proteins were separated according to their isoelectric points. These results indicate that the charges on protein molecules are an important factor in their migration during membrane electrophoresis.

Since cytochrome C with a pI of 9.6 is separated using an organic solvent buffer having a pH of 4.5, this indicates that proteins with pI's that are 5 units away from the pH of the organic solvent buffer can be effectively separated by the present methods.

EXAMPLE 4

Two-Dimensional Membrane Electrophoresis

Human breast carcinoma cell extracts (generously provided by Dr. George Tuszynski of the Dept. of Biology, Temple University) were prepared by low power sonication of the cells for 2-3 seconds, on ice. Four microliters of the extracts containing 6 µg total protein were mixed with 4 µl of caprolactone and spotted at the middle of a PVDF blot membrane (7.5 cm×8 cm). The electrophoresis was performed on the horizontal electrophoresis apparatus with the "sandwich unit" arrangement described in Example 2. The cell extracts were separated in the first dimension at 3.5 kV for 5 minutes (generating a current of about 0.1 mA or about 0.0016 mA/cm$^2$), using Buffer A (pH 4.5).

Upon completion of the first dimension separation, the membrane was marked to ensure proper orientation, and washed two times for several minutes each in deionized water to remove the first dimension solvents. A new filter paper wick was equilibrated with the second dimension Buffer B (pH 8.5) and was placed on top of the bottom plate. After equilibration with the second dimension solvent, the membrane was then placed on top of the new filter paper wick at 90° from its original position and covered with a top plate. The second dimension separation was carried out at 3.5 kV for 5 minutes (generating a current of about 0.4 mA or about 0.007 mA/cm 2). All operations were carried out at room temperature without cooling.

At the end of the second dimension separation, the membrane was removed, washed with water and stained with the Reactive Brown dye as in Example 2. As a comparison, 2-D SDS-PAGE was also performed with 80 μg of the human breast carcinoma cell extract prepared as above. The SDS-PAGE gels were stained with silver stain (a common dye for staining conventional 2-D gels). The amount of cell extract used in the 2-D SDS-PAGE represents more than ten times the amount used in the 2-D membrane electrophoresis. Moreover, the 2-D SDS-PAGE took 2 days to perform, whereas the 2-D membrane electrophoresis was completed in about 30 minutes.

Figure 6A:
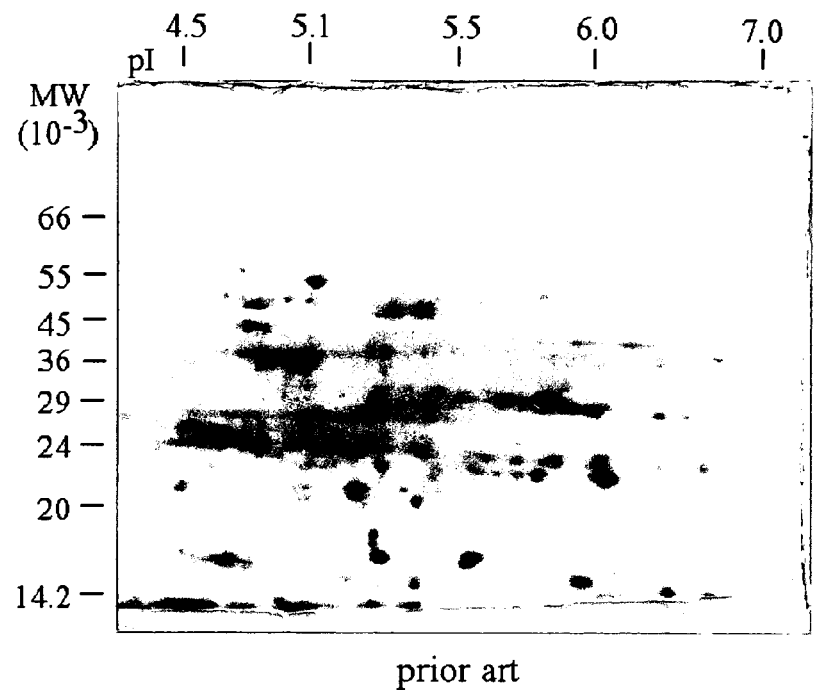
FIG. 6A is a silver stain of a standard two dimensional SDS-PAGE of a human breast carcinoma cell extract. The first dimension is isoelectric focusing (pI), and the second dimension separation by molecular weight in SDS buffer.
Figure 6B:
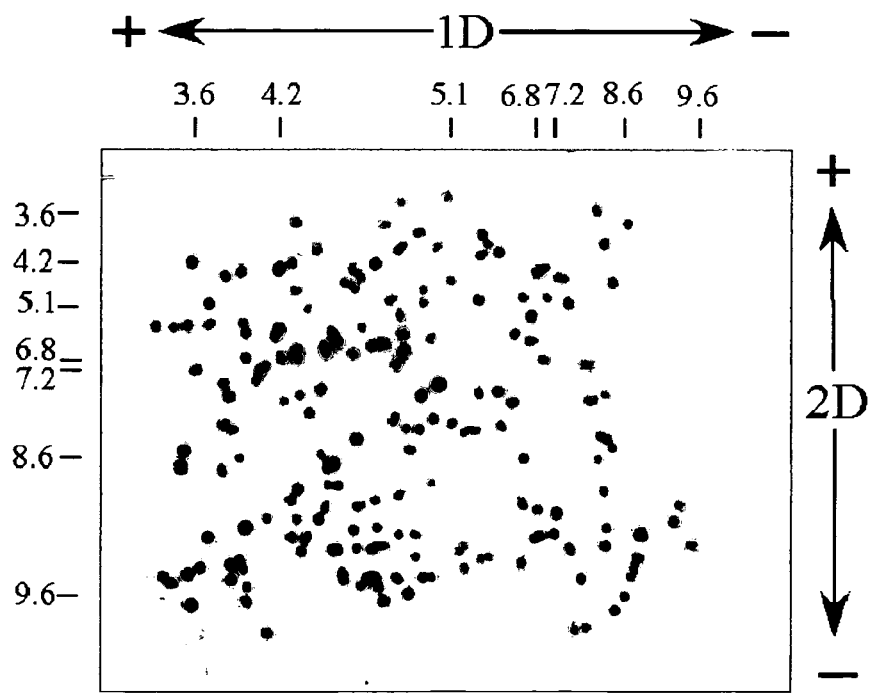
FIG. 6B is a two dimensional membrane electrophoresis of a human breast carcinoma cell extract on a PVDF membrane according to the invention. The first and second dimensions in which the proteins were separated during the membrane electrophoresis are shown, respectively, by "−←1D→+" and "+←2D→−".

The results of the 2-D SDS-PAGE and the 2-D membrane electrophoresis are shown in FIGS. 6A and 6B, respectively. The 2-D membrane electrophoresis shows several hundred clear and well-defined protein spots (FIG. 6B). In contrast, considerably fewer protein spots were visible in the 2-D SDS-PAGE, and those that were visible were diffuse and streaky (FIG. 6A). It is believed that the streaks seen in the 2-D SDS-PAGE separation are due to the migration of poorly-solvated hydrophobic proteins through the gel matrix. These results show that the 2-D membrane electrophoresis represents a significant improvement over the conventional 2-D polyacrylamide gel electrophoresis methods in terms of the time required to complete the separations, the amount of sample required to run the electrophoresis, and the resolution obtained.

EXAMPLE 5

Immunodetection of Allergens with Membrane Electrophoresis

Proteins separated by membrane electrophoresis can be identified by the direct probing of the membrane with antibodies specific for the protein of interest. This was demonstrated by detecting asthma-causing allergens in a *B. germanica* protein extract electrophoresed on a PVDF membrane, as follows.

A 2 cm×8 cm PVDF membrane was spotted with a single 4 μl sample of *B. germanica* dry body part protein extract prepared as in Example 2 (5 μg total protein). The sample was electrophoresed in one dimension as in Example 2, using Buffer B (pH 8.5) at 3.5 kV for five minutes. Following electrophoresis, the membrane was washed thoroughly with deionized water for several minutes to remove excess organic solvents. The membrane was then cut into two halves of 1 cm×8 cm. One half was stained with the Reactive Brown dye as in Example 2, and the other half was subjected to immunodetection as follows.

The membrane half was first washed with Tris-buffered saline containing 0.05% Tween 20, pH 7.4 (TTBS) for 15 minutes. The membrane half was then incubated in 5% nonfat dry milk in TTBS buffer for 2 hours, followed by washing with TTBS for 15 minutes, with one change of TTBS. The membrane half was then incubated overnight in a primary antibody solution (IgE) obtained from pooled sera collected from individuals that were known to have asthmatic symptoms caused by German cockroaches (titer was 1:1,000 dilution). The membrane half was then washed again for at least 30 minutes in TTBS to remove the primary antibody. The membrane half was incubated in a tagged secondary antibody (goat-antihuman IgE) at a titer of 1:5,000 for 2 hours, and then washed again for 30 minutes in TTBS. Visualization of the allergens was carried out by placing the membrane half in a solution of 5-bromo-4-chloro-3-indolyl phosphate and nitro blue tetrazolium (BCIP/NBT). When the allergen bands were of desired intensity, the reaction was stopped with the addition of deionized water.

Figure 7:
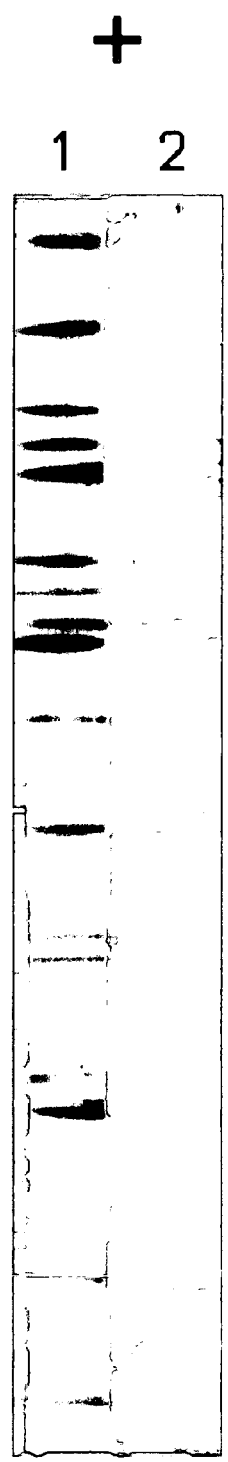
FIG. 7 shows the detection of asthma-causing allergens in *B. germanica* proteins electrophoresed on a PVDF membrane according to the invention. Lane 1 is a Reactive Brown profile of the separated proteins. Lane 2 is an immunostain of the separated proteins showing the allergen bands. The orientation of the membrane with respect to the positive and negative electrodes during electrophoresis is indicated by a "+" and "−".

FIG. 7 shows the protein profile of the membrane half stained with Reactive Brown dye (Lane 1) as compared to the membrane half that had undergone immunodetection (Lane 2). Seven clearly visible and highly separated immunogens are present in the immunostained membrane half, and six can easily be assigned to their corresponding proteins as seen in the Reactive Brown-protein profile. The remaining allergen band was apparently from a protein that was below the limit of detection of the Reactive Brown stain (~1 ng). In separate experiments, pooled sera from individuals that were known to have no asthmatic symptoms were used as controls, and no immunoreactive bands were detected.

EXAMPLE 6

Detection of Protein-Protein Complexes

Protein-protein complexes can be detected after protein samples have been separated by membrane electrophoresis. To demonstrate this, samples containing a trypsin-soybean trypsin inhibitor complex, and samples containing a protease-protease inhibitor complex from the nematode symbiotic bacteria *Photorhabdus luminescens* Hp. were electrophoresed on PVDF membranes as follows.

Preparation of *P. luminescens* Hp Protein Samples—One liter of LB media was inoculated with a single colony of *P. luminescens* Hp and incubated for 7 days with shaking at 28° C. The media was then centrifuged at 7,500×g for 1 hour. The supernatant was collected and concentrated by precipitation with 80% w/v ammonium sulfate, centrifugation at 7,000×g, and resuspension in 10 mM sodium phosphate buffer, pH 6.5. The concentrated culture was dialyzed overnight against water. Protease was purified by benzamidine-agarose affinity chromatography and protease inhibitor was similarly purified by trypsin-agarose affinity chromatography. 5 μl (1 μg protein) of the individual proteins as well as the complex (by mixing protein with its partner for 10 min at room temperature) were applied as spots at the center of a 3 cm×8 cm PVDF membrane. Both trypsin and trypsin inhibitor were obtained from Sigmas Chemical (St. Louis, Mo.). Trypsin and trypsin inhibitor were prepared separately and made to a concentration of 1 mg/ml in water. To obtain the trypsin-trypsin inhibitor complex, the proteins were combined and allowed to incubate for 15 minutes at room temperature.

Figures 8A, 8B:
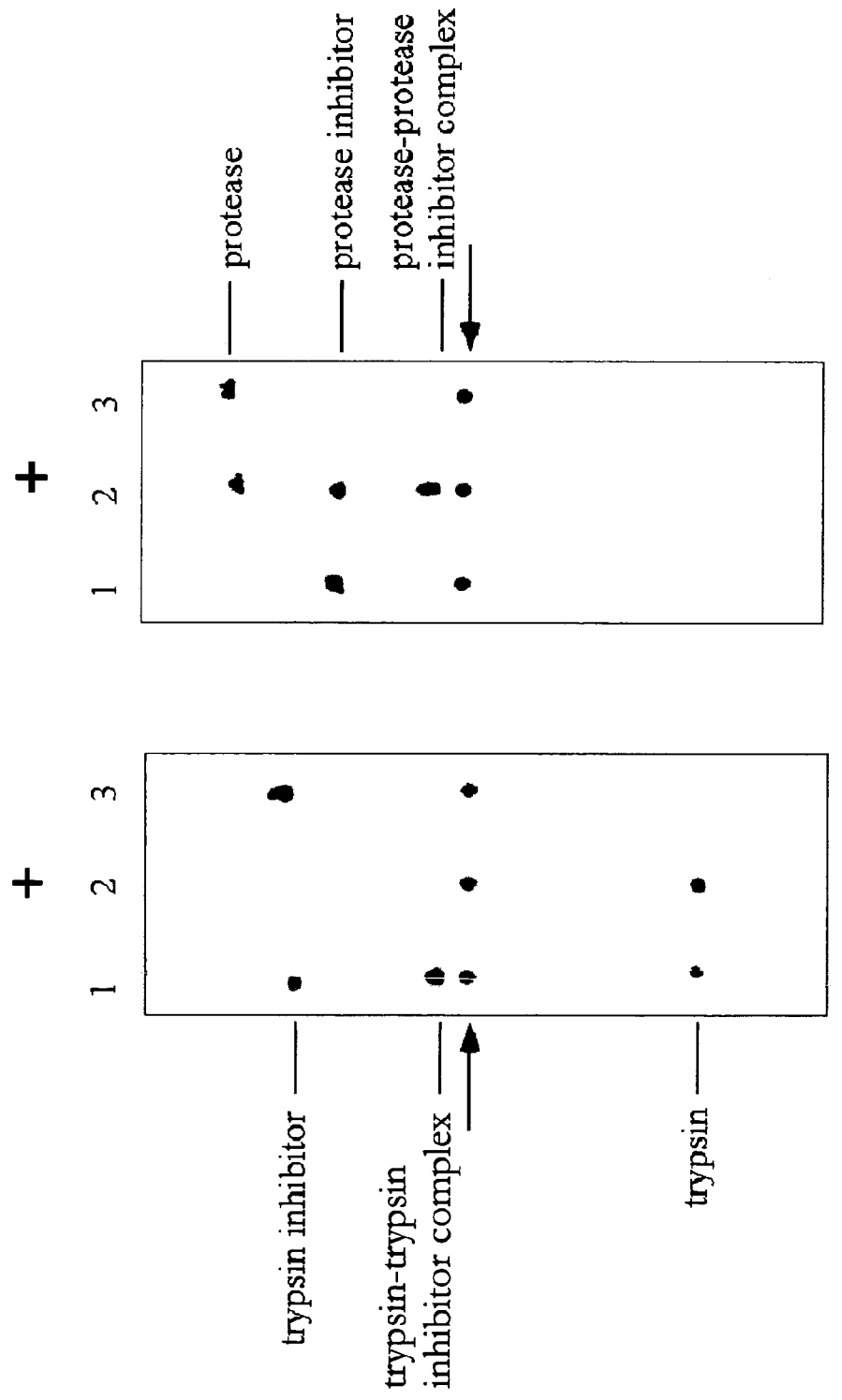
FIG. 8A shows the detection of a trypsin/trypsin inhibitor complex after electrophoresis of the complex on a PVDF membrane according to the invention.
FIG. 8B shows the detection of a protease/protease inhibitor complex after electrophoresis of the complex on a PVDF membrane. The orientation of the membranes with respect to the positive and negative electrodes during electrophoresis is indicated by a "+" and "−". In both figures, the arrow represents the origin.

1-D membrane electrophoresis was performed as in Example 2 at 3.5 kV in Buffer B (pH 8.5) for 5 minutes, at a current of 0.003 mA/cm². After washing the blot membrane with water, the proteins were detected by the Reactive Brown dye method as in Example 2. FIGS. 8A and 8B shows that both the individual protein species and the protein-protein complexes can be detected.

EXAMPLE 7

Detection of Protein-Ligand Interactions

In addition to detecting protein-protein complexes, protein-ligand interactions can also be detected after membrane electrophoresis of protein samples. To demonstrate this, the interaction of β-lactoglobulin A (a fatty acid binding protein) with stearate (a fatty acid) is shown after electrophoresis of sample on a PVDF membrane.

A solution of 1 mg/ml β-lactoglobulin A was prepared in deionized H₂O, and a 0.1 mM zinc-stearate solution was prepared in furfuryl alcohol. One microliter aliquots of the two solutions were mixed, and allowed to incubate for 5 minutes at room temperature to form a protein-ligand complex. Samples containing β-lactoglobulin A (the free protein), zinc-stearate (the free ligand) and the protein-ligand complex were spotted onto a 3 cm×8 cm PVDF membrane. 1-D membrane electrophoresis was performed as in Example 2, at 3.5 kV for 5 minutes in Buffer B (pH 8.5). After electrophoresis, the membrane was stained with the Reactive Brown dye as in Example 2. The results, given in FIG. 9, clearly show that the complex formed β-lactoglobulin A and stearate was easily detected (lane 2). The spot seen on the membrane above the complex is the origin on which the protein samples were spotted.

EXAMPLE 8

Detection of Enzymatic Activity

Detection of enzymatic activity following regular polyacrylamide gel electrophoresis is difficult, because the gels typically contain anionic denaturing agents (e.g., SDS). Also, the lengthy washes necessary to remove the anionic detergents can cause the protein bands in these gels to diffuse. Diffusion of the protein bands can preclude the accurate detection of the enzyme of interest.

In contrast, membrane electrophoresis preserves protein biological activity, and no re-naturing steps are necessary prior to detecting enzyme activity. Enzymes can therefore be rapidly and accurately detected on the membranes after electrophoresis. To demonstrate this, esterase activity was detected in a *B. germanica* protein extract electrophoresed on a 3 cm by 8 cm PVDF membrane as in Example 2, at 3.5 kV for five minutes in Buffer B (pH 8.5).

Figure 10:
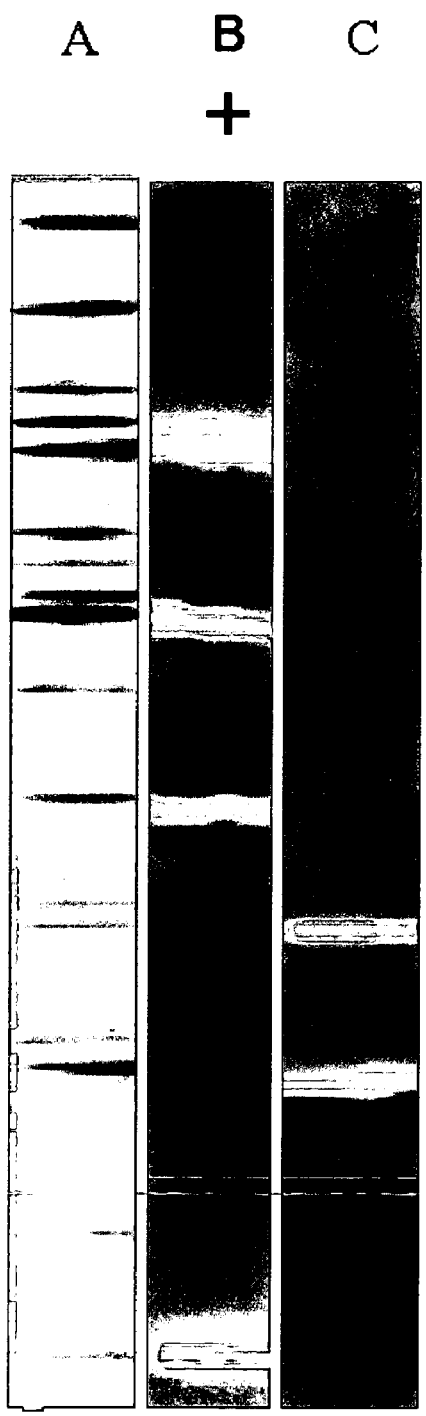
FIG. 10 shows the detection of esterase and protease activity in *B. germanica* proteins electrophoresed on a PVDF membrane according to the invention. Lane A is a Reactive Brown profile of the separated proteins. Lane B is a fluorescent scan of the separated proteins showing the esterase bands. Lane C is a fluorescent scan of the separated proteins showing the protease bands. The orientation of the membrane with respect to the positive and negative electrodes during electrophoresis is indicated by a "+" and "−".

After electrophoresis, the membrane was equilibrated in 0.1 M tris-HCl, pH 7.5 for 20 minutes, with one change of buffer. The membrane was cut into two 1 cm by 8 cm halves. One membrane half was stained with Reactive Brown dye as in Example 2, to provide a *B. germanica* protein profile (FIG. 10, Lane A). The other membrane half was tested for the presence of esterase enzymes by incubation in 7.5 µg/ml 4-methylumbelliferyl butyrate ("4MU-butyrate") for 5 minutes. The esterase on the membrane cleaved the fluorogenic 4MU-butyrate substrate, and produced bands of intense fluorescence containing 4-methylumbelliferone (4MU). The fluorescent bands indicating esterase activity were imaged with an Alpha Imager 2000 digital camera (Alpha Inotech). As shown in FIG. 10, Lane B, five fluorescent esterase bands were visible in the *B. germanica* protein sample.

A similar experiment was conducted in which protease activity was detected in the separated *B. germanica* proteins with 6 µg/ml Nα-carbobenzoxy-L-arginine-7-amido-4-methylcoumarin ("CBZ-arg-7AMC"). CBZ-arg-7AMC is a fluorogenic substrate specific for trypsin-like serine proteases. FIG. 10, Lane C shows two distinct fluorescent bands on the membrane, indicating the presence of proteases in the *B. germanica* protein sample.

EXAMPLE 9

Assessment of Protein Purity and Protein Degradation by 1-D Membrane Electrophoresis A number of therapeutic drugs or vaccines preparations are proteins, or contain protein molecules. During transportation and storage, these protein-containing preparations can degrade or become contaminated. As proteins in the preparation degrade, a signature profile is created which can be used to assess the purity of the preparation and identify possible contaminants.

SDS-PAGE is currently the method of choice for analyzing protein degradation profiles in protein-containing preparations. However, SDS-PAGE is slow, can require large quantities of sample, and often provides poor resolution of separated proteins. As demonstrated by the following experiment, these drawbacks can be avoided by using membrane electrophoresis to analyze protein-containing preparations for degradation.

One milliliter of a preparation containing bovine serum albumin (BSA; 1 mg/ml) was stored at room temperature over a 12 hr period to induce degradation of the protein. Fifty microliters of the BSA preparation was removed at the zero time point and at every hour over the entire period, and frozen for later analysis by 1-D membrane electrophoresis. Electrophoresis was performed as in Example 2 at 3.5 kV for five minutes, using Buffer A (pH 4.5). The results are shown in FIG. 11.

Figure 11:
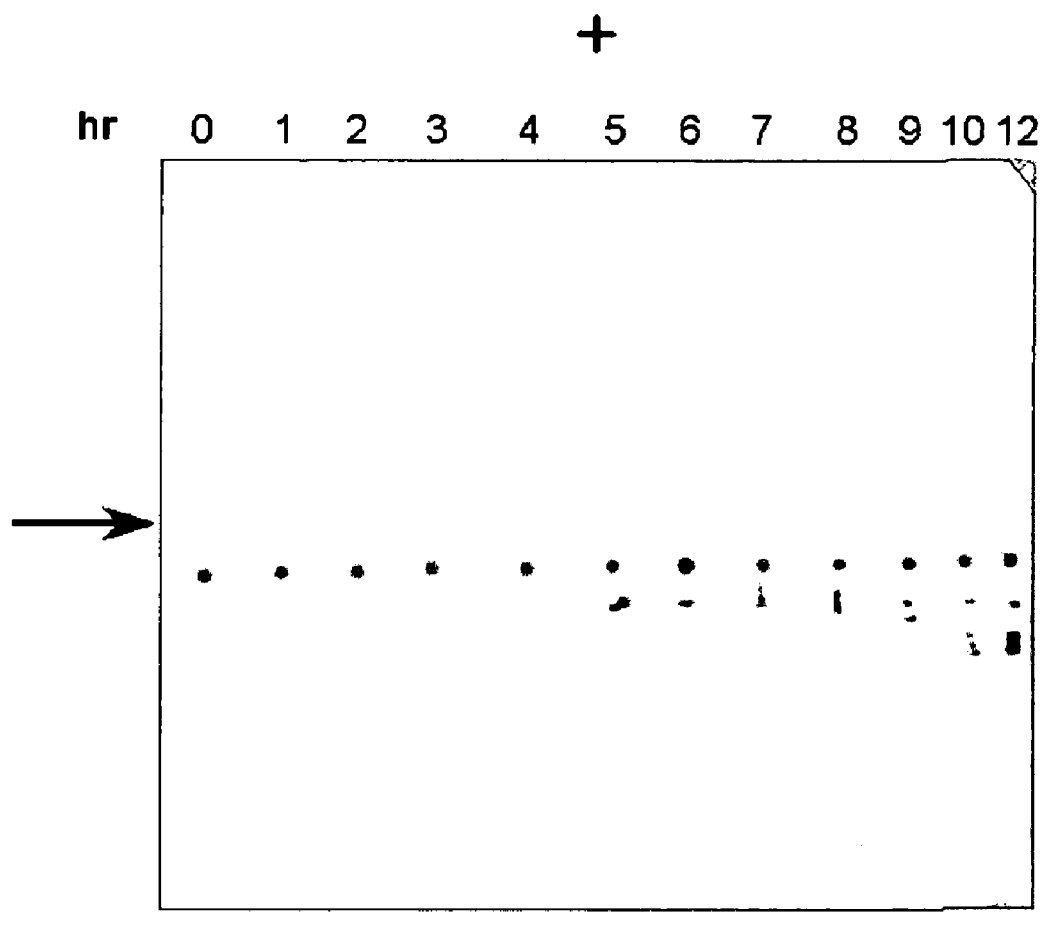
FIG. 11 shows the detection of BSA degradation profiles over time, which were obtained by membrane electrophoresis on a PVDF membrane according to the invention. Samples of BSA kept at room temperature were taken at time zero, and at hourly intervals over a 12-hour period, as indicated in the figure. The origin where the protein samples were spotted is marked with an arrow, and the orientation of the membrane with respect to the positive and negative electrodes during electrophoresis is indicated by a "+" and "−".

From FIG. 11, it can be seen that degradation of BSA occurs after 5 hours exposure to room temperature, and progresses throughout the remainder of the 12 hour period. Unique, high resolution degradation profiles are evident for the 5-6 hour time points, 7-9 hour time points, and 10-12 hour time points. These results indicate that protein degradation can be rapidly and accurately detected in protein preparations by membrane electrophoresis, and suggest that this method could be easily adapted for high throughput screening of large numbers of protein preparations.

EXAMPLES 10a AND 10b

Protein Samples Migrate on the Surface of the Protein Bindiny Membrane During Membrane Electrophoresis

EXAMPLE 10a

Confocal Microscopy of a Protein Binding Membrane in Cross-Section

Six micrograms of a serum protein sample was applied onto a 7.5 cm×8 cm piece of PVDF, as described in Example 2 above. The protein sample was then separated in two dimensions essentially as described in Example 4 above. The first dimension separation was carried out in Buffer A (see Example 1) for 5 min at 3.5 kV. The second dimension was carried out using Buffer B (see Example 1) at 3.5 kV for 5 min. The membrane was then washed for 30 min with two changes of water. The separated protein was covalently labeled with fluorescein-isothiocyanate (FITC) as described in Houston, B., & Peddie, D. Anal. Biochem. 177, 263-267 (1989), the entire disclosure of which is herein incorporated by reference. Following the covalent labeling procedure, the membrane was washed to remove any excess FITC which could cause unwanted background fluorescence. The separated proteins were visible as yellow fluorescent spots under UV illumination.

A medium sized spot was excised from the membrane and was cut in cross-section so that the cut bisected the protein spot. One half of the bisected spot was fixed in paraffin wax on a depression microscope slide, so that the PVDF membrane was perpendicular to the slide. The depression in the slide was then filled with water and a coverslip was placed over the sample. Using confocal microscopy, the fluorescent-labeled protein was seen to be only on the surface of the membrane.

EXAMPLE 10b

Electrophoresis with the Sample Side of the Protein Binding Membrane Entirely in Contact with the Filter Paper Wick Two identically-spotted PVDF membranes were separately subjected to 1D membrane electrophoresis, using Buffer A (see Example 1). One membrane was electrophoresed as in Example 3 above, with the sample side facing up against the top glass plate (i.e., not in contact with the filter paper wick). The other membrane had the sample side face-down against the filter paper wick, rather than facing up against the top glass plate. In the former arrangement, the membrane is referred to as "right side up." In the latter arrangement, the membrane is referred to as being "upside down."

On the "upside down" membrane, the lightly stained protein bands visible on the "right side up" membrane were missing. Also, the more heavily stained bands were more diffused on the "upside down" membrane than on the "right side up" membrane. These results indicate that, during membrane electrophoresis, proteins are on the surface of the membrane. The less abundant proteins are thus lost to the filter paper wick, and the more abundant protein became diffused due to competition between membrane surface and the filter paper wick. Complete loss of the more abundant proteins was not seen because proteins bind more tightly to the surface of PVDF than to the filter paper.

EXAMPLE 11

Separation of Hydrophilic and Hydrophobic Proteins via 2-D Membrane Electrophoresis To demonstrate that the newly developed 2-D membrane electrophoresis can separate not only hydrophilic but also hydrophobic proteins, human serum proteins were fractionated into both hydrophilic and hydrophobic fractions using Triton X-114 following the procedure of Bordier (*J. Biol. Chem.* 256. 1604-1607, 1981), the entire disclosure of which is herein incorporated by reference. A 5 µl aliquot of serum was treated with 200 µl of a solution containing 1% Triton X-114, 10 mM Tris-HCl (pH 8.0) and 100 mM NaCl at 4° C. The solution was then incubated at 25° C. for 10 min. The resulting cloudy solution was spun at 10,000×g at 25° C. for 10 min. The aqueous top phase and the bottom detergent droplet were separated. The process was repeated to ensure clean separation of the two protein fractions. Excess detergent was removed from both phases by spinning the fractions through a Biogel P-6 micro-spin column before analysis by 2-D membrane electrophoresis as follows.

Figure 12B:
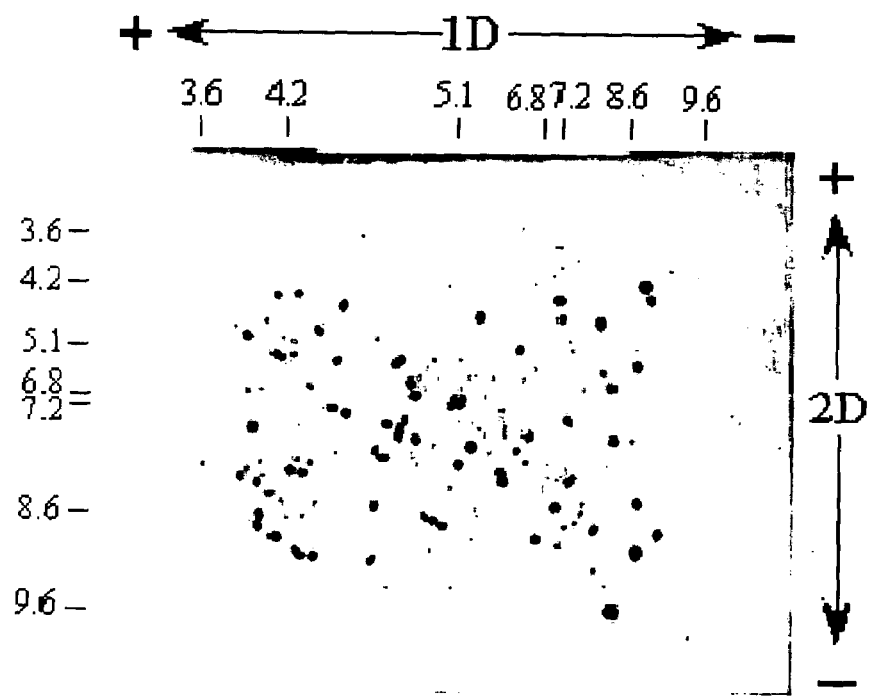

Each sample was diluted to 12 mg/ml with deionized water before an equal volume of caprolactone was added. Six micrograms of each sample were separately loaded onto the center of a 7.5 cm×8 cm piece of PVDF membrane. 2-D membrane electrophoresis was carried out on each sample using Buffer A (see Example 1) in the first dimension for 5 min at 0.1 mA and 3.5 kV, and Buffer B (see Example 1) in the second dimension for 5 min at 0.4 mA and 3.5 kV as described previously. Following protein separation, the membranes were washed in deionized water for at least 20 min with two changes of water and silver stained. As shown in FIG. 12B, the hydrophobic serum proteins were separated into exceptionally clean and well resolved spots (i.e. no diffusion and no streaking as is commonly observed with 2-D PAGE). The hydrophilic serum proteins were also clearly resolved (see FIG. 12A).

All documents referred to herein are incorporated by reference. While the present invention has been described in connection with the preferred embodiments and the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

We claim:

1. An electrophoresis system for the separation of proteins, comprising:
   (i) at least one low conductivity organic solvent buffer comprising at least one base solvent, at least one conductivity enhancer, and optionally at least one conductivity suppressor;
   (ii) a polymeric membrane having high-protein binding capacity, which membrane is compatible with the at least one low conductivity organic solvent buffer; and
   (iii) an electrophoresis apparatus which comprises at least one electrophoresis unit for containing the buffer and membrane, and a power supply capable of generating an electric current in the at least one electrophoresis unit
   wherein the base solvent is ethylene cyclic carbonate or a mixture of propylene carbonate and ethylene cyclic carbonate.

2. The electrophoresis system of claim 1, wherein the at least one base solvent is present in the low conductivity organic solvent buffer in a final concentration of about 1% to about 80%.

3. The electrophoresis system of claim 1, wherein the at least one base solvent is present in the low conductivity organic solvent buffer in a final concentration of about 20% to about 50%.

4. The electrophoresis system of claim 1, wherein the at least one conductivity enhancer is selected from the group consisting of formamide; acetamide; propionamide; butyramide; N-methyl formamide; N-methyl acetamide; N-methyl propionamide; N-methyl butyramide; benzamide; toluamide; lactamide; nicotinamide; 2-furaldehyde; furfuryl alcohol; tetrahydrofurfuryl alcohol; salicylaldehyde; guaiacol; phenol; boric acid; fumaric acid; piperazine; and mixtures thereof.

5. The electrophoresis system of claim 1, wherein the low conductivity organic solvent buffer comprises at least one conductivity suppressor.

6. The electrophoresis system of claim 5, wherein the at least one conductivity suppressor is selected from the group consisting of dimethyl derivatives of formamide and acetamide; 1,3-butanediol; N-methyl pyrrolidinone; sorbitol; glycerol; caprolactone; methoxyethanol; and mixtures thereof.

7. The electrophoresis system of claim 6, wherein at the least one conductivity suppressor is a mixture of 1,3-butanediol, dimethyl formamide and dimethyl acetamide.

8. The electrophoresis system of claim 6, wherein the at least one conductivity suppressor is a mixture of 1,3-butanediol and N-methyl pyrrolidinone.

9. The electrophoresis system of claim 6, wherein the at least one conductivity suppressor is 1,3-butanediol.

10. The electrophoresis system of claim 1, wherein the at least one low conductivity organic solvent buffer has a pH of about pH 3 to about pH 10.

11. The electrophoresis system of claim 1, wherein the membrane is a hydrophobic membrane.

12. The electrophoresis system of claim 11, wherein the hydrophobic membrane comprises a polymer selected from the group consisting of fluorinated polymers; polyolefins; polystyrene or substituted polystyrenes; polysulfones; polyethersulfones; polyesters; polyacrylates; polycarbonates; polyurethane; vinyl polymers; polyacrylonitriles; and mixtures thereof.

13. The electrophoresis system of claim 12, wherein the fluorinated polymer is polyvinylidene difluoride (PVDF).

14. The electrophoresis system of claim 12, wherein the polyolefins are polyethylene, polypropylene, or polymethylpentene.

15. The electrophoresis system of claim 12, wherein the polymer is a polyester and is selected from the group of polyesters consisting of polyethylene terephthalate and polybutylene terephthalate.

16. The electrophoresis system of claim 12, wherein the polymer is a vinyl polymer and said vinyl polymer is polyvinyl chloride.

17. The electrophoresis system of claim 11, wherein the hydrophobic membranes comprise butadiene-styrene copolymer or fluorinated ethylene-propylene copolymer.

18. The electrophoresis system of claim 1, wherein the membrane is a hydrophilic membrane.

19. The electrophoresis system of claim 18, wherein the hydrophilic membrane comprises a polymer selected from the group consisting of nylons; polyimides; polyesters; polyvinyl alcohols; polyvinylamines; polybenzylamides; polyvinylimidazolines; polydiallylamines; and mixtures thereof.

20. The electrophoresis system of claim 19, wherein the hydrophilic membrane comprises a nylon polymer.

21. The electrophoresis system of claim 20, wherein the nylon polymer has about 0.4 moles to about 2 moles amino end groups per mole of nylon.

22. The electrophoresis system of claim 1, wherein the membrane binds at least about 20 µg protein/cm$^2$.

23. The electrophoresis system of claim 1, wherein the membrane binds at least about 50 µg protein/cm$^2$.

24. The electrophoresis system of claim 1, wherein the membrane binds 100 µg protein/cm2 to about 400 µg protein/cm$^2$.

25. The electrophoresis system of claim 1, wherein the membrane is about 0.01 mm thick to about 3 mm thick.

26. The electrophoresis system of claim 25, wherein the membrane is about 0.10 mm thick to about 0.5 mm thick.

27. The electrophoresis system of claim 1, wherein the electrophoresis apparatus comprises a plurality of electrophoresis units.

28. The electrophoresis system of claim 1, wherein the at least one electrophoresis unit is a vertical electrophoresis unit.

29. The electrophoresis system of claim 1, wherein the at least one electrophoresis unit is a horizontal electrophoresis unit.

30. An electrophoresis system for the separation of proteins, comprising:
    (i) at least one low conductivity organic solvent buffer comprising at least one base solvent, at least one conductivity enhancer, and optionally at least one conductivity suppressor;
    (ii) a polymeric membrane having high-protein binding capacity, which membrane is compatible with the at least one low conductivity organic solvent buffer; and
    (iii) an electrophoresis apparatus which comprises at least one electrophoresis unit for containing the buffer and membrane, and a power supply capable of generating an electric current in the at least one electrophoresis unit
    wherein the at least one conductivity enhancer is a mixture of salicylaldehyde and furfuryl alcohol, or a mixture of formamide and 2-furaldehyde, or a mixture of formamide and furfuryl alcohol, or a mixture of formamide and tetrahydrofurfuryl alcohol.

31. The electrophoresis system of claim 30, wherein the at least one conductivity enhancer is present in the low conductivity organic solvent buffer in a final concentration of about 0.1% to about 50%.

32. The electrophoresis system of claim 30, wherein the at least one conductivity enhancer is present in the low conductivity organic solvent buffer in a final concentration of about 5% to about 30%.

33. A method for the two-dimensional electrophoretic separation of proteins, comprising the steps of:
    (1) providing an electrophoresis system comprising:
        (i) a first low conductivity organic solvent buffer having a first pH and a second low conductivity organic solvent buffer having a second pH;
        (ii) a membrane having a high protein binding capacity and which is compatible with the first and second organic solvent buffers; and
        (iii) an electrophoresis apparatus which comprises at least one electrophoresis unit for containing the first and second organic solvent buffers and membrane;
    (2) applying at least one sample comprising proteins to be separated to the membrane;
    (3) placing the membrane and the first organic solvent buffer in the at least one electrophoresis unit, wherein the membrane is placed in a first orientation;
    (4) separating the proteins in a first dimension by generation of an electric current in the at least one electrophoresis unit;
    (5) replacing the first organic solvent buffer in the at least one electrophoresis unit with the second organic solvent buffer;
    (6) placing the membrane in the at least one electrophoresis unit in a second orientation; and
    (7) separating the proteins in a second dimension by generation of an electric current in the at least one electrophoresis unit.

34. The method of claim 33, wherein the membrane is washed to remove the first organic solvent buffer after separating the proteins in a first dimension.

35. The method of claim 33, wherein the first and second organic solvent buffers have the same composition.

36. The method of claim 33, wherein the electrophoresis unit is a horizontal electrophoresis unit.

37. The method of claim 33, wherein the electrophoresis apparatus comprises a plurality of electrophoresis units.

38. The method of claim 33, wherein the two-dimensional electrophoresis is performed under non-denaturing conditions.

39. The method of claim 38, further comprising the step of detecting enzymatic activity in the separated proteins.

40. The method of claim 38, further comprising the step of detecting protein-binding interactions in the separated proteins.

41. The method of claim 40, wherein the protein-binding interactions comprise the formation of protein-protein complexes.

42. The method of claim 41, further comprising the step of identifying the proteins in the protein-protein complexes.

43. The method of claim 40, wherein the protein-binding interactions comprise protein-ligand interactions.

44. The method of claim 40, wherein protein-binding interactions in the separated proteins are detected by a mobility shift of at least one of the separated proteins.

45. The method of claim 33, further comprising the step of detecting the separated proteins with at least one antibody.

46. An electrophoresis system for the separation of proteins, comprising:
(i) at least one low conductivity organic solvent buffer comprising at least one base solvent, at least one conductivity enhancer, and at least one conductivity suppressor, wherein the at least one conductivity suppressor is selected from the group consisting of dimethyl derivatives of formamide and acetamide; 1,3-butanediol; N-methyl pyrrolidinone; sorbitol; glycerol; caprolactone; methoxyethanol; and mixtures thereof;
(ii) a polymeric membrane having high-protein binding capacity, which membrane is compatible with the at least one low conductivity organic solvent buffer; and
(iii) an electrophoresis apparatus which comprises at least one electrophoresis unit for containing the buffer and membrane, and a power supply capable of generating an electric current in the at least one electrophoresis unit.

47. The electrophoresis system of claim 46, wherein the at the least one conductivity suppressor is present in the low conductivity organic solvent buffer in a final concentration of about 0.1% to about 50%.

48. The electrophoresis system of claim 46, wherein the at the least one conductivity suppressor is present in the low conductivity organic solvent buffer in a final concentration of about 5% to about 30%.

49. The electrophoresis system of claim 46, wherein the at least one low conductivity organic solvent buffer has a pH of about pH 3 to about pH 10.

50. The electrophoresis system of claim 46, wherein the membrane is a hydrophobic membrane.

51. The electrophoresis system of claim 50, wherein the hydrophobic membrane comprises a polymer selected from the group consisting of fluorinated polymers; polyolefins; polystyrene or substituted polystyrenes; polysulfones; polyethersulfones; polyesters; polyacrylates; polycarbonates; polyurethane; vinyl polymers; polyacrylonitriles; and mixtures thereof.

52. The electrophoresis system of claim 46, wherein the membrane is a hydrophilic membrane.

53. The electrophoresis system of claim 52, wherein the hydrophilic membrane comprises a polymer selected from the group consisting of nylons; polyimides; polyesters; polyvinyl alcohols; polyvinylamines; polybenzylamides; polyvinylimidazolines; polydiallyamines; and mixtures thereof.

54. A method for the electrophoretic separation of proteins, comprising the steps of:
(1) providing at least one low conductivity organic solvent buffer comprising at least one base solvent, at least one conductivity enhancer, and at least one conductivity suppressor selected from the group consisting of dimethyl derivatives of formamide and acetamide; 1,3-butanediol; N-methyl pyrrolidinone; sorbitol; glycerol; caprolactone; methoxyethanol; and mixtures thereof;
(2) providing a polymeric membrane having high-protein binding capacity, which membrane is compatible with the at least one low conductivity organic solvent buffer;
(3) applying at least one sample comprising proteins to be separated to the membrane; and
(4) separating the proteins by electrophoresis.

55. The method of claim 54, wherein the proteins are separated in a first dimension.

56. The method of claim 54, wherein the proteins are separated in first dimension, and subsequently separated in a second dimension.

57. The method of claim 54, wherein the electrophoresis is performed under non-denaturing conditions.

58. The method of claim 57, further comprising the step of detecting enzymatic activity in the separated proteins.

59. The method of claim 58, wherein the enzymatic activity is detected with a colorimetric or a fluorogenic substrate.

60. The method of claim 57, further comprising the step of detecting protein-binding interactions in the separated proteins.

61. The method of claim 60, wherein an antibody is added to the sample before electrophoresis.

62. The method of claim 61, wherein the antibody is labeled with a detection agent.

63. The method of claim 62, wherein the detection agent is selected from the group consisting of colored dyes; fluorescent dyes; chemiluminescent labels; biotinylated labels; radioactive labels; affinity labels; and enzyme labels.

64. The method of claim 60, wherein the protein-binding interactions comprise protein-ligand interactions.

65. The method of claim 64, wherein a ligand is added to the sample before electrophoresis.

66. The method of claim 65, wherein the ligand is labeled with a detection agent.

67. The method of claim 66, wherein the detection agent is selected from the group consisting of colored dyes; fluorescent dyes; chemiluminescent labels; biotinylated labels; radioactive labels; affinity labels; enzyme labels; and protein-specific antibodies.

68. The method of claim 60, wherein protein-binding interactions in the separated proteins are detected by a mobility shift of at least one of the separated proteins.

69. The method of claim 54, further comprising the step of detecting the separated proteins with at least one antibody.

70. The method of claim 69, wherein the antibody is labeled with a detection agent.

71. The method of claim 70, wherein the detection agent is selected from the group consisting of colored dyes; fluorescent dyes; chemiluminescent labels; biotinylated labels; radioactive labels; affinity labels; and enzyme labels.

72. The method of claim 71, further comprising the step of detecting protein-binding interactions in the separated proteins.

73. The method of claim 72, wherein the protein-binding interactions comprise the formation of protein-protein complexes.

74. The method of claim 54, wherein the current generated in the electrophoresis unit is about 0.0001 mA/cm$^2$ membrane to about 0.2 mA/cm$^2$ membrane.

75. The method of claim 54, wherein the current generated in the electrophoresis unit is about 0.0005 mA/cm$^2$ membrane to about 0.05 mA/cm$^2$ membrane.

76. The method of claim 54, wherein the current generated in the electrophoresis unit is about 0.001 mA/cm$^2$ membrane to about 0.025 mA/cm$^2$ membrane.

77. The method of claim 54, wherein the electrophoresis unit is a horizontal electrophoresis unit.

78. The method of claim 54, wherein the at least one protein sample comprises a plurality of samples taken at different time points from a protein-containing preparation.

79. The method of claim 78, wherein the electrophoresis produces a degradation profile for the protein-containing preparation.

80. The method of claim 54, wherein the at least one protein sample is obtained from an organism at least two different time points.

81. The method of claim 54, wherein the electrophoresis is performed in the absence of a pH gradient.

82. The method of claim 81, wherein the proteins are separated in a first dimension.

83. The method of claim 81, wherein the proteins are separated in first dimension, and subsequently separated in a second dimension.

84. The method of claim 81, wherein the electrophoresis is performed under non-denaturing conditions.

85. The method of claim 84, further comprising the step of detecting enzymatic activity in the separated proteins.

86. The method of claim 84, further comprising the step of detecting protein-binding interactions in the separated proteins.

87. The method of claim 86, wherein the protein-binding interactions comprise the formation of protein-protein complexes.

88. The method of claim 87, further comprising the step of identifying the proteins in the protein-protein complexes.

89. The method of claim 86, wherein the protein-binding interactions comprise protein-ligand interactions.

90. The method of claim 86, wherein protein-binding interactions in the separated proteins are detected by a mobility shift of at least one of the separated proteins.

91. An electrophoresis system for the separation of proteins, comprising:
  (i) at least one low conductivity organic solvent buffer comprising at least one base solvent, at least one conductivity enhancer, and optionally at least one conductivity suppressor;
  (ii) a polymeric membrane having high-protein binding capacity, which membrane is compatible with the at least one low conductivity organic solvent buffer; and
  (iii) an electrophoresis apparatus which comprises at least one horizontal electrophoresis unit for containing the buffer and membrane, and a power supply capable of generating an electric current in the at least one horizontal electrophoresis unit, wherein the at least one horizontal electrophoresis unit comprises:
    (1) a first and a second independent buffer chamber;
    (2) a top plate and a bottom plate of substantially similar length and width bridging the first and a second independent buffer chambers, wherein the membrane is sandwiched between the top and bottom plates; and
    (3) a wick with a first and a second end disposed between the bottom plate and the membrane, wherein the wick is longer than the top and bottom plates such that the first and second wick ends extend into the first and a second independent buffer chambers, respectively.

92. A method for the electrophoretic separation of proteins, comprising the steps of:
  (1) providing at least one low conductivity organic solvent buffer comprising at least one base solvent, at least one conductivity enhancer, and at least one conductivity suppressor;
  (2) providing a polymeric membrane having high-protein binding capacity, which membrane is compatible with the at least one low conductivity organic solvent buffer;
  (3) applying at least one sample comprising proteins to be separated to the membrane, wherein the at least one sample is mixed with a wetting agent comprising ε-caprolactone; and
  (4) separating the proteins by electrophoresis.

93. An electrophoresis system for the separation of proteins, comprising:
  (i) at least one low conductivity organic solvent buffer comprising at least one base solvent, at least one conductivity enhancer, and optionally at least one conductivity suppressor;
  (ii) a polymeric membrane having high-protein binding capacity, which membrane is compatible with the at least one low conductivity organic solvent buffer; and
  (iii) an electrophoresis apparatus which comprises at least one electrophoresis unit for containing the buffer and membrane, and a power supply capable of generating an electric current in the at least one electrophoresis unit;
  wherein the membrane is a hydrophobic membrane comprising a polymer selected from the group consisting of polyethylene terephthalate, polybutylene terephthalate, butadiene-styrene copolymer, and fluorinated ethylene-propylene copolymer.

* * * * *